US008000775B2

(12) United States Patent
Pogue et al.

(10) Patent No.: US 8,000,775 B2
(45) Date of Patent: *Aug. 16, 2011

(54) SYSTEMS AND METHODS FOR TOMOGRAPHIC IMAGE RECONSTRUCTION

(75) Inventors: Brian William Pogue, Hanover, NH (US); Daqing Piao, Stillwater, OK (US); Keith D. Paulsen, Hanover, NH (US); Shudong Jiang, Hanover, NH (US); Hamid Dehghani, Exeter (GB); Heng Xu, Union City, CA (US); Roger Springett, Hanover, NH (US); Subhadra Srinivasan, Keene, NH (US)

(73) Assignee: The Trustees of Dartmouth College, Hanover, MA (US)

( * ) Notice: Subject to any disclaimer, the term of this patent is extended or adjusted under 35 U.S.C. 154(b) by 417 days.

This patent is subject to a terminal disclaimer.

(21) Appl. No.: 12/088,845

(22) PCT Filed: Apr. 27, 2006

(86) PCT No.: PCT/US2006/016210
§ 371 (c)(1),
(2), (4) Date: Apr. 8, 2009

(87) PCT Pub. No.: WO2006/116672
PCT Pub. Date: Nov. 2, 2006

(65) Prior Publication Data
US 2009/0247847 A1 Oct. 1, 2009

Related U.S. Application Data

(60) Provisional application No. 60/689,727, filed on Jun. 10, 2005.

(51) Int. Cl.
*A61B 6/00* (2006.01)

(52) U.S. Cl. .................................. 600/473; 600/310
(58) Field of Classification Search .......... 600/473–478, 600/309, 310
See application file for complete search history.

(56) References Cited

U.S. PATENT DOCUMENTS

| 4,515,165 A | 5/1985 | Carroll |
| 5,349,954 A | 9/1994 | Tiemann et al. |
| 5,447,159 A | 9/1995 | Schultz |

(Continued)

FOREIGN PATENT DOCUMENTS

WO WO03012391 2/2003

OTHER PUBLICATIONS

PCT/US2006/016210 International Search Report, mailed Dec. 18, 2006, 5 pages.

(Continued)

*Primary Examiner* — Sanjay Cattungal
(74) *Attorney, Agent, or Firm* — Lathrop & Gage LLP

(57) ABSTRACT

Optical tomography systems that provide light of multiple distinct wavelengths from a plurality of sources are described. The systems direct light into mammalian tissue, and light from the mammalian tissue is collected at a plurality of reception points. Collected light from each reception point is separated according to its wavelength, and received by a photodetector to produce path attenuation signals representing attenuation along paths between the source locations and the reception points. An image construction system generates a tomographic image of the mammalian tissue from the path attenuation signals. One embodiment of an optical imaging system includes an optical coherence tomography-near infrared probe. The systems and methods may utilize a spectral derivative approach that provides insensitivity to the boundary and boundary artifacts in the signal, thereby improving the quality of the reconstructed images.

13 Claims, 15 Drawing Sheets

U.S. PATENT DOCUMENTS

| | | | |
|---|---|---|---|
| 5,692,511 | A | 12/1997 | Grable |
| 5,694,938 | A * | 12/1997 | Feng et al. .................. 600/425 |
| 5,722,407 | A | 3/1998 | Klingenbeck-Regn et al. |
| 6,195,580 | B1 | 2/2001 | Grable |
| 6,324,418 | B1 | 11/2001 | Crowley et al. |
| 6,615,063 | B1 | 9/2003 | Ntziachristos et al. |
| 6,662,042 | B1 | 12/2003 | Grable |
| 6,903,825 | B2 | 6/2005 | Tualle |
| 7,047,057 | B2 * | 5/2006 | Hall et al. .................... 600/407 |
| 7,133,138 | B2 * | 11/2006 | Horii et al. ................... 356/497 |
| 7,231,243 | B2 | 6/2007 | Tearney et al. |
| 7,383,076 | B2 * | 6/2008 | Ntziachristos et al. ....... 600/473 |
| 2003/0085338 | A1 * | 5/2003 | Hall et al. .................. 250/208.1 |
| 2003/0107742 | A1 | 6/2003 | Tualle |

OTHER PUBLICATIONS

PCT/US2006/016210 International Preliminary Report on Patentability, mailed Nov. 8, 2007, 8 pages.

Piao, D., et al. "Video-rate near-infrared optical tomography using spectrally-encoded parallel light delivery" (submitted to Optics Letters, 2005).

Brooksby, B., et al. "Magnetic Resonance-Guided Near-Infrared Tomography of the Breast" Review of Scientific Instruments, 75(12) 5262-5270 (2004).

Xu, H., et al., An MRI-coupled Broad-band Near Infrared Tomography System for Small Animal Brain Studies Applied Optics, Apr. 10, 2005 Issue.

McBride, et al. "A Parallel-detection frequency-domain near-infrared tomography system for hemoglobin imaging of the breast in vivo" Review of Scientific Instruments 72(3) 1817-24, Mar. 2001.

Pogue BW, et al. "Comparison of imaging geometries for diffuse optical tomography of tissue." Opt Express 4(8), 270-286, 1999.

Pogue, B. W., et al. "Instrumentation and design of a frequency-domain diffuse optical tomography imager for breast cancer detection." Optics Express, 1(13), 394-403 (1997).

U.S. Appl. No. 11/115,865, Office Action mailed Apr. 6, 2009, 6 pages.

U.S. Appl. No. 11/115,865, Response to Office Action filed Dec. 30, 2008, 11 pages.

U.S. Appl. No. 11/115,865, Office Action mailed Sep. 30, 2008, 7 pages.

U.S. Appl. No. 11/115,865, Response to Office Action filed Apr. 4, 2008, 4 pages.

U.S. Appl. No. 11/115,865, Office Action mailed Jan. 4, 2008, 6 pages.

* cited by examiner

Varying Hemoglobin in inclusion

Varying Scattering in inclusion

SYSTEMS AND METHODS FOR TOMOGRAPHIC IMAGE RECONSTRUCTION

RELATED APPLICATIONS

This application claims priority to U.S. application Ser. No. 11/115,865, filed Apr. 27, 2005, and to U.S. Application No. 60/689,727, filed Jun. 10, 2005, each of which is incorporated herein by reference.

U.S. GOVERNMENT RIGHTS

This invention was made with Government support under grants NIH RO1 NS39471, U54 CA105480, PO1CA80139, RO1CA69544, 1R21CA100984-01A1 and K25 CA106863 awarded by the National Institutes of Health, and DAMD17-03-01-0405 awarded by the Department of Defense. The U.S. Government has certain rights in this invention.

BACKGROUND

Diffuse Optical Tomography (DOT) is a technique wherein tissue is illuminated at multiple source points on a tissue surface with electromagnetic energy having wavelengths ranging from visible light to near infrared (NIR). Light transmitted through the tissue from each source point is then detected at each of multiple reception points on the tissue surface to measure attenuation and scattering along paths from each source point to each reception point. Scattering is mainly the result of light interactions with solid or semi-solid masses, whereas attenuation of the radiation over the pathlength may be caused by absorption and/or emission. For example, light is absorbed by compounds (chromophores) within the tissue, such as hemoglobin, myoglobin, lipids and water, that interact with electromagnetic energy of a particular wavelength. Emission—radiation of energy from a molecule—can result from naturally occurring fluorescent and bioluminescent molecules and/or from medical imaging compositions in the tissue.

Measuring and modeling of attenuation and scattering allows for the creation of potentially high contrast images. For example, the heme group of myoglobin and/or hemoglobin absorbs visible and near infrared radiation, and the spectral characteristics of the absorption vary noticeably with the degree of oxygenation. Therefore, high contrast may be obtained between portions of the tissue containing high concentrations of heme (such as blood and muscle) and portions of tissue containing low concentrations of heme (such as fat), and between highly oxygenated and poorly oxygenated or infarcted tissues. In particular, the high vascularity in tumors provides an elevated hemoglobin content and a potentially high intrinsic optical contrast between the tumor and normal tissue.

Modeling of the tissue is typically performed with a computerized tissue model having parameters that are adjusted such that modeled tissue matches the measured attenuation and scattering along each path. In some models, chromophore concentrations and scatter parameters are determined by comparing absolute transmission data to known (signature) spectra. Such systems are subject to large noise contributions and errors, such as variations between source and detector coupling coefficients, boundary reflection mismatches, and inaccurate geometric modeling. These errors arise because the systems attempt to match model-calculated data with calibrated measurement data, which often contains these coupling/boundary errors.

Spectrally-constrained models, such as Direct Chromophore Spectral Reconstruction (DCSR), show improved accuracy and are more robust in the presence of noise than conventional models, because they use coupled spectral information to constrain the reconstruction. DCSR is, however, subject to some of the same measurement errors as traditional methods, namely, coupling coefficient and external boundary variations, as well as inaccurate geometric modeling. See, for example, Srinivasan, S.; Pogue, B. W.; Jiang, S.; Dehghani, H.; Paulsen, K. D. "Spectrally Constrained Chromophore and Scattering NIR Tomography Provides Quantitative and Robust Reconstruction", Applied Optics, 44(10), 1858-1869, (2004) and Corlu, A.; Durduran, T.; Choe, R.; Schweiger, M.; Hillman, E. M. C.; Arridge, S. R.; Yodh, A. G. "Uniqueness and Wavelength Optimization in Continuous-Wave Multispectral Diffuse Optical Tomography", Optics Letters, 28(23), 2339-2341, (2003). The parameterized tissue model is projected onto one or more hypothetical image planes, which are prepared as two-dimensional cross-sectional slices and/or three-dimensional images.

Systems for optical tomography, similar to that described in C. H. Schmitz, M. Löcker, J. M. Lasker, A. H. Hielscher, and R. L. Barbour, "Instrumentation for fast functional optical tomography," Rev. Sci. Instr., 73(2): 429-439 (2002), have been marketed by NIRx Medical Technologies, LLC of Glen Head, N.Y. The system marketed by NIRx can resolve 5-millimeter lesions 3 centimeters below the skin surface. The system of Schmitz mechanically distributes light from a single laser into multiple illumination points spaced over the tissue to be studied in succession. As each illumination point is illuminated, light received at multiple reception points spaced over the tissue is measured. With the apparatus of Schmitz, data for approximately 3 image planes per second can be acquired.

The amount of heme at a particular soft-tissue location can, however, vary rapidly, so that acquisition of data at a rate of 3 image planes per second may be insufficient to accurately detect a physiological occurrence or anomaly. For example, both elastic and muscular arteries, including associated pathology such as aneurysms, may enlarge and shrink with each heartbeat. Active muscle and brain tissue not only is known to consume oxygen at an activity-dependent rate, thereby changing its spectral characteristics, but it releases local vasoactive substances such as adenosine with resulting activity-dependent vasodilation occurring in seconds. Vasculature in different tissue types, such as tumor and surrounding tissue, can also respond differently to exogenous vasoactive substances. Similarly, since the corpora cavernosa may undergo rapid changes in heme content and oxygenation, imaging of those changes could be of interest in the study, diagnosis and treatment of erectile dysfunction or priapism.

The degree of oxygenation and heme content of soft tissue regions under varying conditions can be of interest to a physician attempting to diagnose disease. For example, it is known that many malignant tumors require so much oxygen that portions of the tumor may become ischemic and necrotic despite their increased vascularity. Much heart disease is ischemic, as are many strokes. Peripheral vascular disease, often implicated in diabetic foot ulcers, often produces—sometimes activity-dependent—inadequate blood flow and abnormal zones of ischemia in peripheral tissue such as limb tissue. These zones of ischemia tend to be more prone to forming slow or non-healing ulcers than normally oxygenated tissue. Accurate imaging of vessel obstructions and ischemia in tissue may allow for more successful debridement of ulcers and permit success with other treatments such as revascularization. Imaging of rapid activity-dependent changes in regional distribution of heme content and oxygenation of brain tissue could be of interest in research into brain function, as well as in the diagnosis of a wide variety of neurological conditions including epilepsy.

It is desirable to have a short acquisition time to measure the dynamic aspects of heme distribution, also known as hemodynamics. It has been proposed that scattering and attenuation for multiple paths can be acquired simultaneously using intensity modulation encoding of the source. Franceschini (Francheschini et al, "Frequency-domain techniques enhance optical mammography: Initial clinical results" Proc Natl Acad Sci USA. 94(12): 6468-6473, 1997) demonstrated this approach with a frequency domain source, and the concept was further developed by Siegel (Siegel, A M, Marota, J J A and Boas, D A. "Design and evaluation of a continuous-wave diffuse optical tomography system." Optics Express 4:287-298, 1999) for a continuous wave source based system. Siegel developed a system where several source points are illuminated at the same time. Light applied to each simultaneously-illuminated source point is amplitude modulated such that light from that source point can be distinguished from light applied to other simultaneously-illuminated source points, by having a different modulation frequency. For example, if one source point is amplitude-modulated with a first tone, and a second source point is amplitude-modulated with a second tone, light received at a reception point can be distinguished by measuring a ratio between the first and second tone in modulation as received at the reception point.

SUMMARY

In one embodiment, a tomography system, includes: a plurality of lasers of a first group, each laser of the first group for generating light of a distinct wavelength within a first wavelength band; apparatus for applying the light from lasers of the first group to mammalian tissue at laser-specific locations; apparatus for collecting light from the mammalian tissue at a plurality of reception points; apparatus for separating light received from the apparatus for collecting light according to a wavelength of the received light; apparatus for generating a path attenuation signal encoding received light amplitude information for each reception point at each wavelength corresponding to each laser of the plurality of lasers; and image construction apparatus for receiving the path attenuation signal and for reconstructing a tomographic image of the mammalian tissue.

In one embodiment, a method of generating tomographic images of mammalian tissue includes: generating infrared light of a plurality of laser-specific wavelengths in a first narrow band of wavelengths; applying the infrared light to a plurality of laser-specific locations on the mammalian tissue; receiving infrared light from a plurality of reception points on the mammalian tissue; separating received light from each reception point of the plurality of reception points according to wavelength into separated received light; transducing the separated received light into electronic signals; and constructing a tomographic image of attenuation in the mammalian tissue from the electronic signals.

In one embodiment, a software product includes computer-readable instructions, stored on computer-readable media, wherein the instructions, when executed by a computer, perform steps for creating a tomographic image of tissue. The instructions include instructions for obtaining data from a detector indicative of light intensity, instructions for determining the difference in the ratio of intensity for multiple wavelengths at one or more source-detector pairs, instructions for using the difference data to reconstruct structural and functional data of the tissue, and instructions for creating a tomographic image of the tissue. Instructions for determining emission source concentration may also be included.

In another embodiment, a software product includes computer-readable instructions, stored on computer-readable media, wherein the instructions, when executed by a computer, perform steps for creating a tomographic image of tissue. The instructions include instructions for obtaining data from a detector indicative of light intensity, instructions for determining the difference in the ratio of intensity for multiple wavelengths at one or more source-detector pairs, instructions for determining emission source concentration, and instructions for creating a tomographic image of the tissue.

In another embodiment, a method of creating an image of living mammalian tissue includes collecting spectral intensity data from multiple source-detector pairs, using Spectral Derivative Image Reconstruction (SDIR) to manipulate the data, and using the SDIR manipulated data in an image reconstruction model to obtain a reconstructed image of the tissue.

In another embodiment, a software product includes computer-readable instructions, stored on computer-readable media, wherein the instructions, when executed by a computer, perform steps for creating a tomographic image of tissue. The instructions include instructions for obtaining frequency-domain data from a detector indicative of transmitted light intensity, instructions for using the ratio of light intensity for multiple wavelengths at one or more source-detector pairs in a spectrally-constrained algorithm to reconstruct structural and functional data of the tissue, and instructions for creating a tomographic image of the tissue.

DETAILED DESCRIPTION

It has been found that the spectral characteristics of chromophores and scatterers within mammalian tissue are sufficiently broad that, if visible or near-infrared light from a group of single-mode lasers is used to interrogate tissue with small wavelength separation between lasers, radiation from each laser suffers levels of attenuation and scattering largely similar to radiation from the other lasers of the group.

When lasers at separate wavelengths are associated with different source positions, a spectral encoding of source origin occurs in a way that can be detected and decoded in parallel at any reception point.

Figure 1:
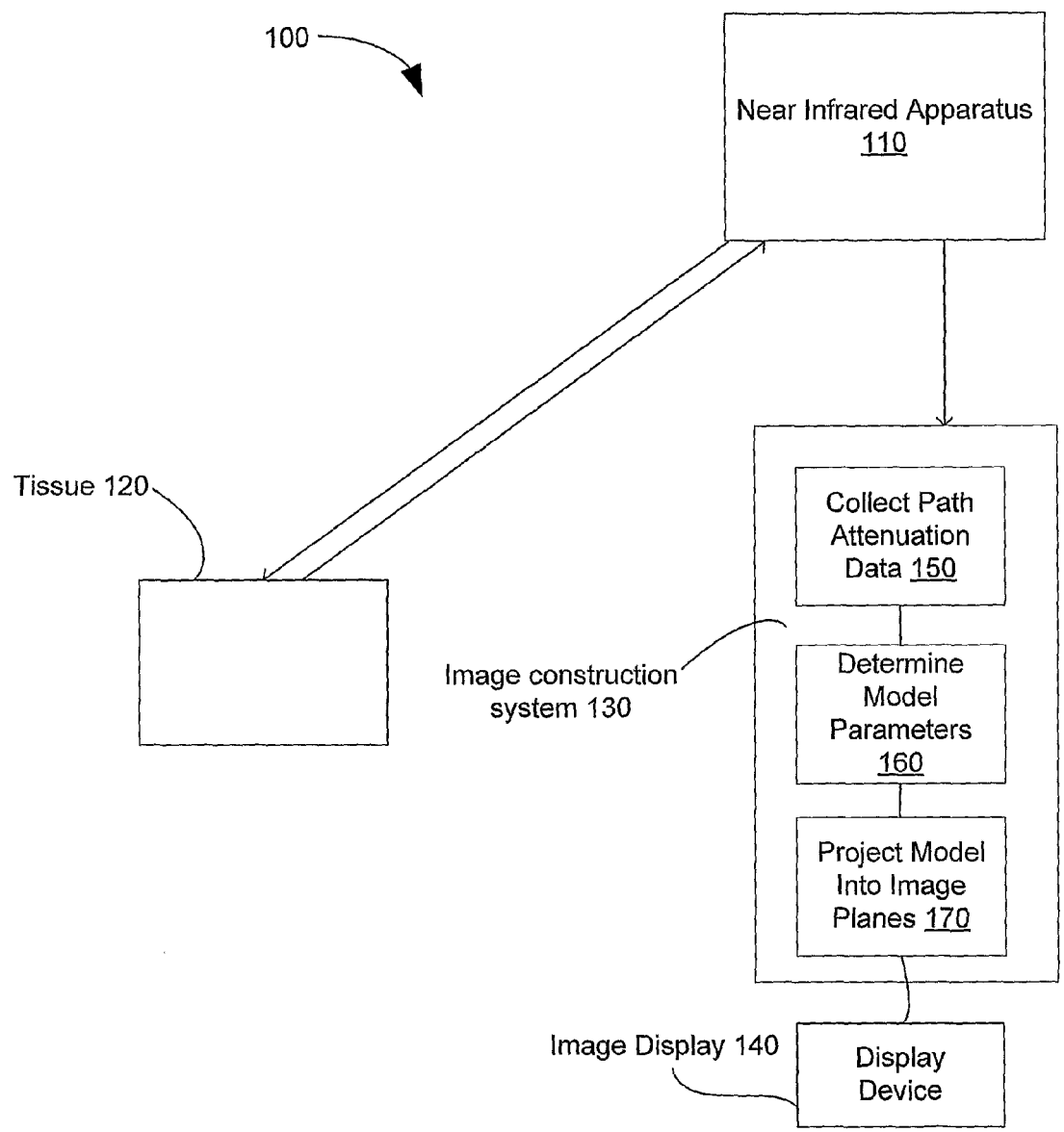
FIG. 1 is a block diagram of a spectral-encoding system for high-rate hemodynamic tomography, according to an embodiment.

FIG. 1 shows a spectral-encoding system 100 for high-rate hemodynamic tomography. System 100 includes a near infrared apparatus 110, mammalian tissue 120, an image construction system 130, and an image display 140. A tissue model, or phantom, may be used in place of tissue 120 during development and calibration. Near infrared apparatus 110 generates path attenuation data 150 from tissue 120. The image construction system 130 is configured to receive path attenuation data 150 from near infrared apparatus 110 and construct an image of tissue 120 on image display 140. Image construction system 130 collects tissue-dependent path attenuation data 150 from near infrared apparatus 110, determines voxel attenuation parameters of a tissue model 160, and projects 170 the voxel attenuation parameters into tomographic image planes to generate tomographic images for display on image display 140 using algorithms known in the art. Images are also recorded for later study.

Figure 2:
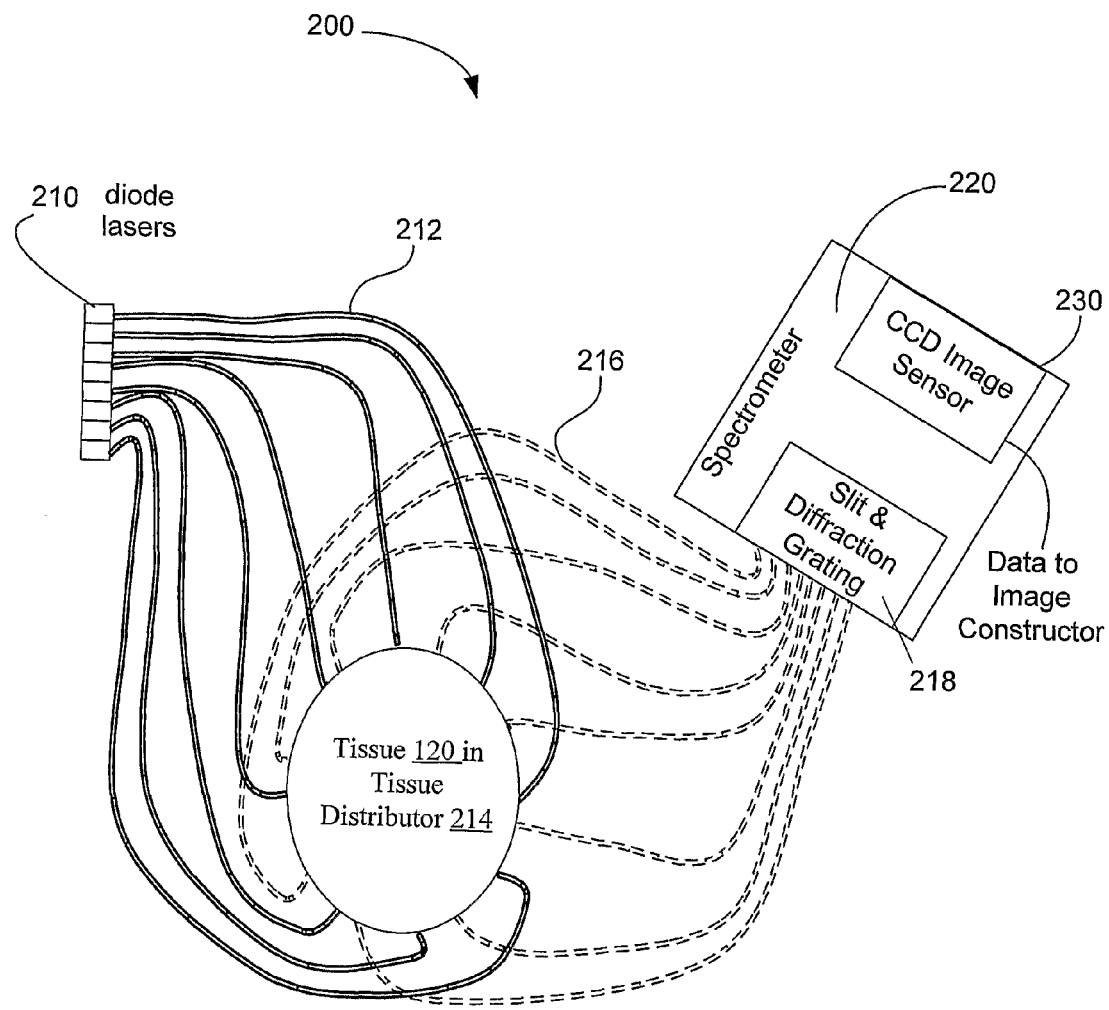
FIG. 2 is a simplified block diagram of a near infrared apparatus of FIG. 1.

FIG. 2 is an abbreviated schematic 200 of the near infrared apparatus 110 of FIG. 1. In an embodiment, near infrared apparatus 110 includes eight diode lasers 210, a spectrometer 220 and a CCD 230. Spectral encoding of diode lasers is achieved by using a number of lasers each operating upon a distinct wavelength in the same spectral band, preferably spaced 0.5 to 1 nm apart within a 4 nm to 10 nm nominal bandwidth. It is anticipated that tighter laser spacing will be used in future versions of the apparatus, especially in embodiments having more lasers. Each diode laser of the eight diode lasers 210 illuminates tissue 120 at laser-specific locations through transmit optic fibers 212 and tissue distributor 214 simultaneously. Light from each laser of lasers 210 is applied at a different location along the periphery of tissue.

Light from lasers 210 penetrates tissue 120. Some of this light is absorbed in the tissue, some is scattered. Light is received from tissue 120 through tissue distributor 214 and receive optic fibers 216 into spectrometer 220. Receive optic fibers 216 are arranged along light entry slit 218 of spectrometer 220, such that light from each fiber 216 enters at a separate location along entry slit 218. Light admitted through entry slit 218 passes through a diffraction grating, and is spread into its spectral components as it is projected onto a charge-coupled device (CCD) image sensor 230. Signals from CCD image sensor 230 are transmitted to image construction system 130 of FIG. 1. Signals from CCD image sensor 230 encode received light amplitude for each reception point at each wavelength corresponding to each of lasers 210.

Light from each receive optic fiber 216 may, and often does, include light scattered through tissue 120 from more than one of lasers 210. Since lasers 210 operate on separate wavelengths, the diffraction grating of spectrometer 220 separates these wavelengths, such that light received from each laser 210 through each receive optic fiber 216 illuminates a separate location on CCD image sensor 230.

Figure 3:
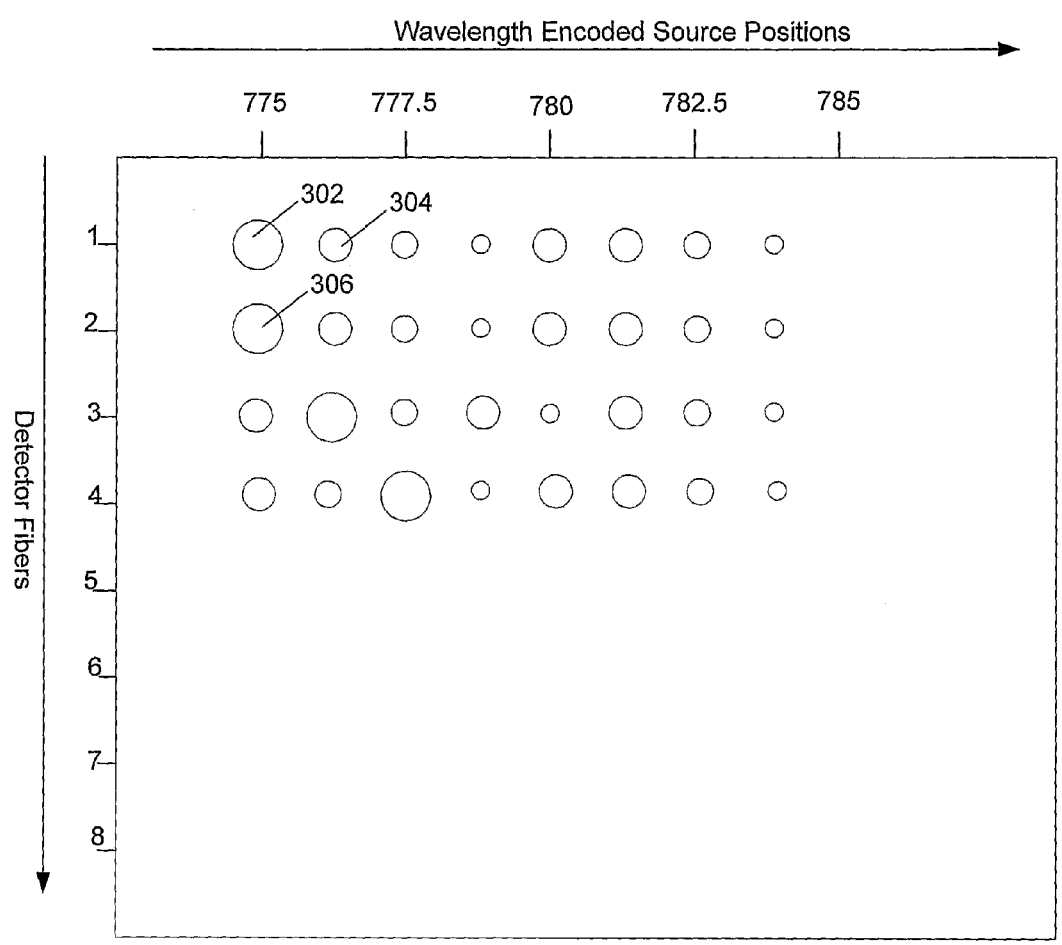
FIG. 3 is a schematic image of light intensities viewed by a CCD chip of the near infrared apparatus of FIG. 2.

Since light from each receive optic fiber 216 enters spectrometer 220 at a separate location along entry slit 218, the CCD image sensor 230 is illuminated with a light pattern similar to that illustrated in FIG. 3. Light originating at a first laser of lasers 210(1) and received through a first fiber 216(1) arrives at location 302. Light received through the first fiber 216(1) but originating from a second laser of lasers 210(2) arrives at a second location 304, and light originating from the first laser of lasers 210(1) and received through a second fiber of fibers 216(2) arrives at a third location 306 on the CCD image sensor 230. While this received light pattern is used by image construction system 130 to construct an image of tissue 120, the received light pattern is not directly an image of tissue 120.

In an embodiment, CCD image sensor 230 of FIG. 2 has an array of 512×512 separate sensor elements, each capable of transducing near infrared or visible light into a signal. Signals from the separate sensor elements correspond to path attenuation information and are encoded into a CCD output signal for use by image construction system 130. It is anticipated that the present apparatus will function with CCD image sensors 230 of other array sizes, particularly those having a greater number of sensor elements.

For monochrome imaging of heme concentration, it is desirable that each laser of lasers 210 be close, preferably within one percent, to a center wavelength of a selected wavelength range so that scattering of each laser is similar to the other lasers. It is also desirable that the center wavelength be close to 800-810 nm, because at this wavelength heme light absorption is similar for oxygenated and deoxygenated hemoglobin. Useful images are obtainable if the center wavelength lies between 620 and 1000 nm.

In a particular embodiment, each of lasers 210 is within the wavelength band of 775.0 to 785.0 nm; hence each laser's bandwidth is less than two percent of its center wavelength, but lasers 210 are spaced apart in that band by approximately 1.2 nm, and each is within fifty nm of 800-810 nm. In an embodiment, the diode lasers 210 are capable of 50 mW each. The lasers are mounted on thermoelectric coolers such that laser operating wavelengths are stable.

In near infrared apparatus 110 a spatially-varying neutral density filter is interposed between lasers 210 and transmit fibers 212 to even out the intensity of illumination, compensating for variations in laser power. Similarly, a spatially-varying neutral density filter is interposed between receive fibers 216 and slit 218 to compensate for variations in receive fiber coupling from tissue 120.

In an alternative embodiment, not shown, there are sixteen receive fibers 216 instead of the eight previously discussed. It is anticipated that the present apparatus is operable with, and may provide improved resolution with, other and greater numbers of receive fibers.

It has been found that sufficient data for images of rodent crania can be acquired in 10 milliseconds while operating the lasers at 10 mW. It is anticipated that imaging oxygen saturation and heme concentration of the human brain cortex may require operation at between 1-100 mW, for 10 to 50 ms. These capture times can support imaging at video rates.

Specific applications in which the system could be used include: imaging blood pulsation in tissue, to assess disease or response to therapy; monitoring uptake or retention of drugs which are optically absorbing or scattering; detection of epidural and subdural hematomas and active intracranial bleeding; imaging of breast tumors and response of the tumor to external stimuli such as different breathing gases, applied pressure, and/or vascular flow changes; imaging fast temporal changes in blood flow in response to an injected drug, such as monitoring peripheral vascular disease response to a drug, or tissue ischemia response to a drug; and uptake and wash out of vascular or tissue maker drugs.

For imaging of heme oxygenation as well as heme concentration, it is desirable that there be two groups of illumination source lasers, a short wavelength group and a long wavelength group. Lasers of each group should operate at a wavelength near to a center wavelength of the group. Both groups of lasers should operate in the 620 to 1000 nanometer band, but the center wavelengths for the groups should be spaced apart. Spacing the center wavelengths between five and fifteen percent wavelength apart will provide resolution of oxygenation.

Figure 4:
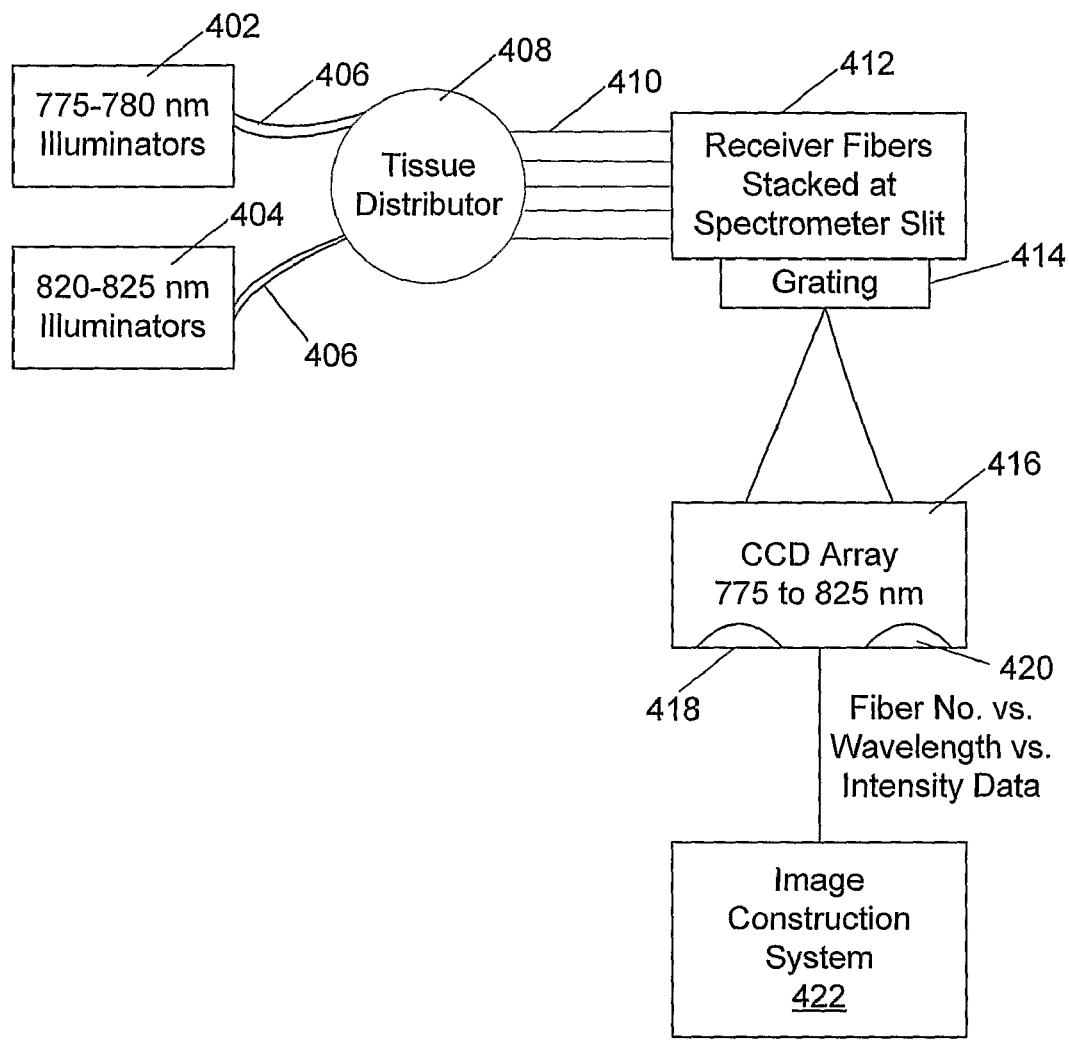
FIG. 4 is a block diagram of a system for imaging oxygen saturation, according to an embodiment.

In another, dichrome, embodiment as illustrated in FIG. 4, suitable for imaging oxygen saturation in tissue as well as heme concentration in tissue, there are eight diode lasers of a first group 402 having wavelengths spaced in the band from 775 to 780 nm, spaced approximately 0.5 nm apart, and eight diode lasers of a second group 404 having wavelengths spaced 0.5 nm apart in the band of 820 to 825 nm. The center wavelengths of the first group and second group are therefore separated by approximately six percent, and each group is less than one percent wide.

Near infrared light from the diode lasers of both groups 402, 404 is coupled through transmit fibers 406 and tissue distributor 408 into mammalian tissue under study. Light from the mammalian tissue under study is coupled from tissue distributor 408 through receive fibers 410 into spectrometer slit 412 and spectrometer diffraction grating 414. After passage through diffraction grating 414, the light is projected onto a CCD sensor array 416. Light originating in the first group of lasers 402 arrives at laser-and-reception fiber specific locations in a first region 418 of CCD sensor array 416. Light originating in the second group of lasers 404 arrives at laser-and-reception fiber specific locations in a second region 420 of CCD sensor array 416. The CCD sensor array 416 is periodically scanned, pixel exposure information is digitized, and the digitized data is transferred to an image construction system 422. In this embodiment, CCD sensor array 416 is a 2048×1024 pixel array. It is anticipated that filters are provided to reduce sensitivity of the sensor array 416 to stray incident light, such as visible light, outside the band of interest.

Image construction system 422 receives digitized data from CCD sensor array 416 and uses information from the first region 418 of the array to construct an image of heme of a first "color". Image construction system 422 also uses information from the second region 420 of CCD sensor array 416 to construct an image of heme of a second "color". At any one region of mammalian tissue, the ratio of light absorption by heme in the first band to absorption by heme in the second band is dependent upon oxygen saturation of heme in that region of tissue. The first "color" and second "color" images are therefore compared to produce an image of oxygen saturation in various portions of the tissue present in the tissue distributor 408.

In an alternative embodiment, two CCD sensor arrays 416 are used, one receives light originating in the first group of lasers 402, the second receives light originating in the second group of lasers 404.

Figure 5:
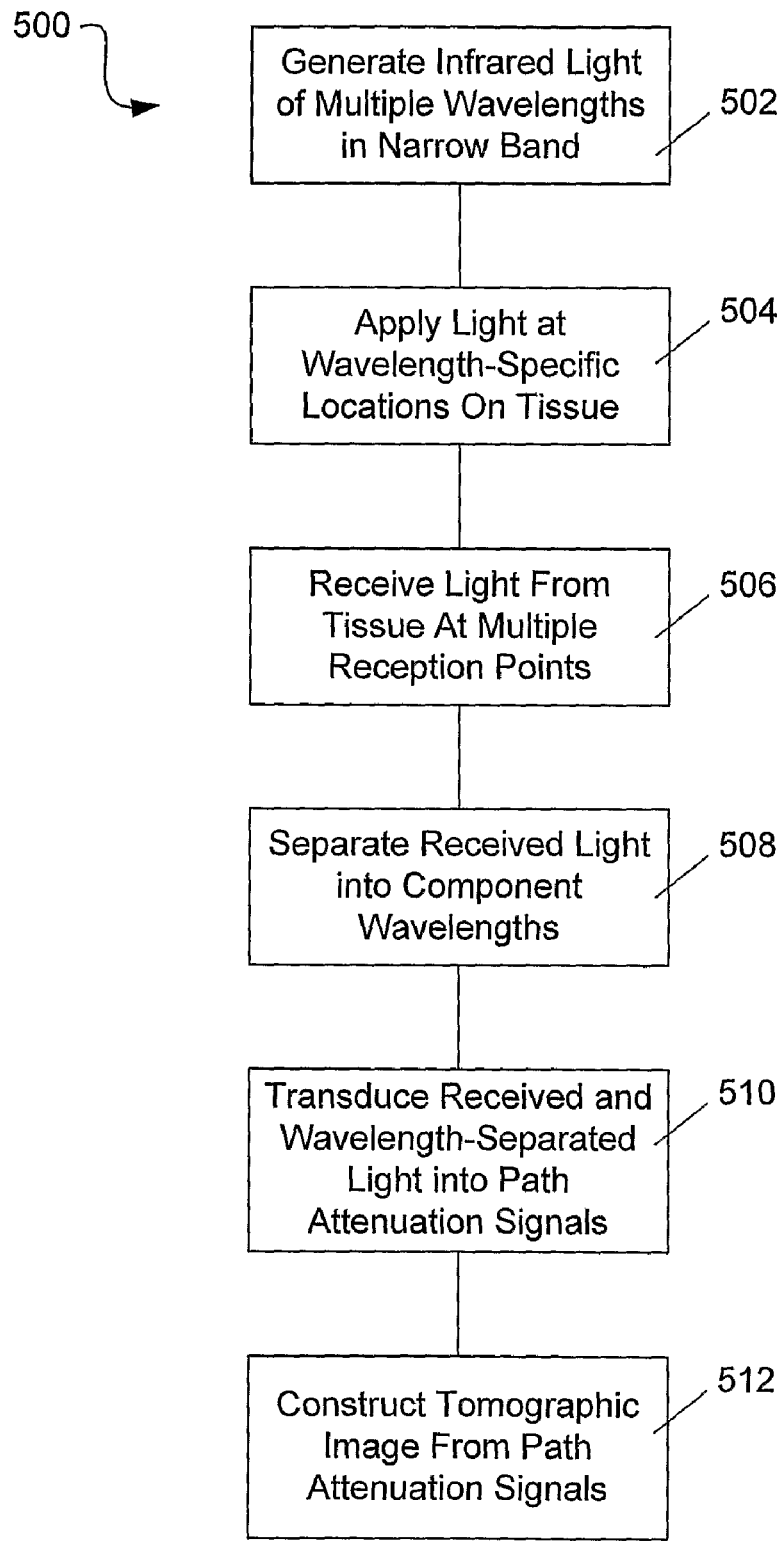
FIG. 5 is a flowchart illustrating a method for spectral-encoding for video-rate hemodynamic tomography, according to an embodiment.

FIG. 5 illustrates a flowchart 500 of a method for constructing tomographic images of heme concentrations in tissue. With reference to FIGS. 1 and 2, near infrared apparatus 110 includes a group of laser light sources 210 for generating 502 infrared light of laser-specific wavelengths in a narrow band of wavelengths. Light from these lasers 210 is collected and applied 504 to mammalian tissue 120 through transmit fibers 212 and tissue distributor 214, then light from tissue 120 is received 506 through tissue distributor 214 and receive fibers 216 at multiple reception points on tissue 120. Light received 506 from tissue is separated 508 by spectrometer 220 into its component wavelengths, each wavelength corresponding to a specific laser of laser light sources 210, while maintaining separation according to receive point. This light is transduced 510 by CCD sensor 230 into electronic signals corresponding to path attenuation. The electronic signals corresponding to path attenuation are input to an image construction system 130, where a tomographic image of the tissue is constructed 512 as previously described.

Figure 6:
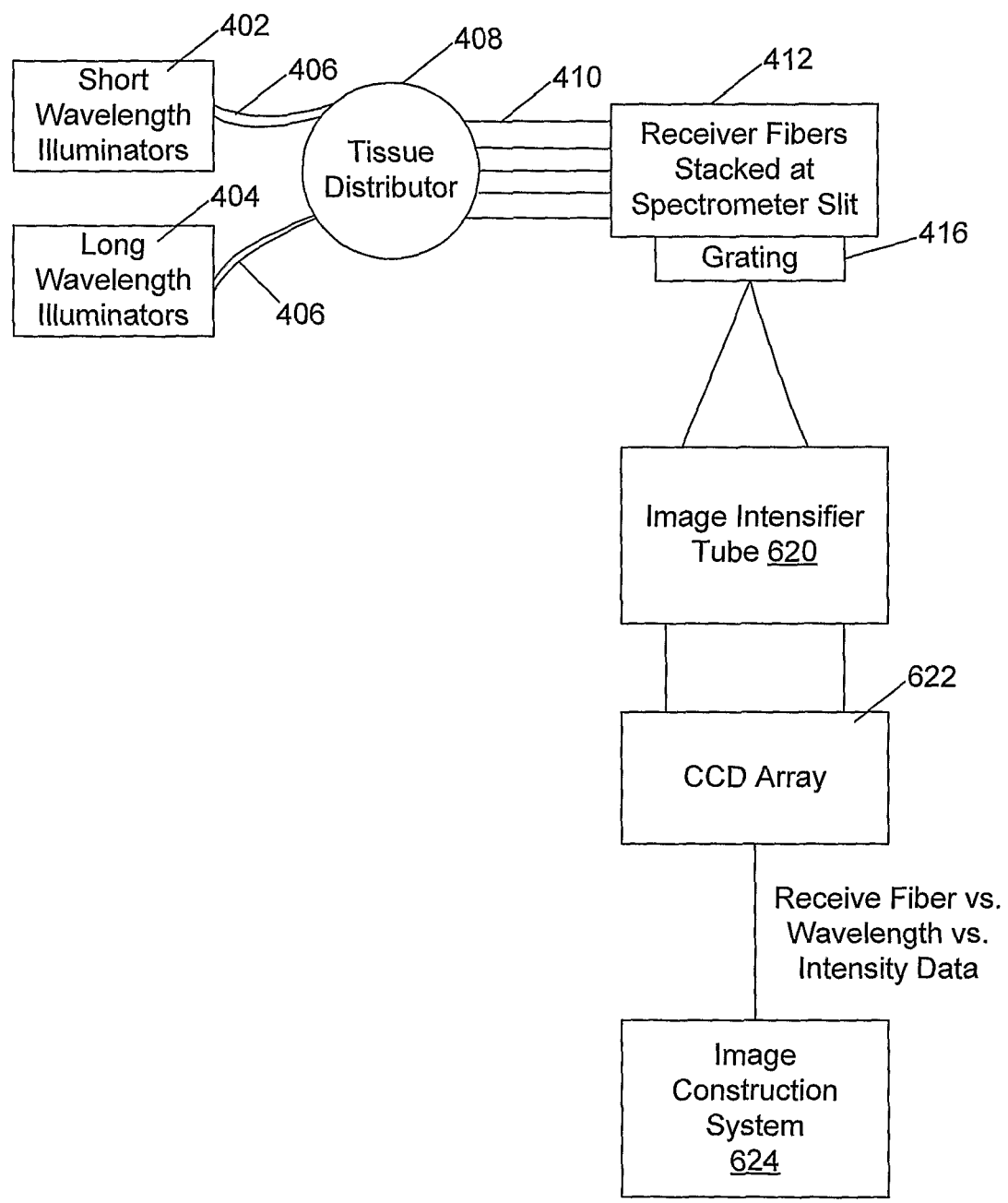
FIG. 6 is a block diagram of an embodiment incorporating an image intensifier tube for improved weak-signal gain.

It can be desirable to have high photodetector gain when imaging structures deep in mammalian tissue. The embodiment illustrated in FIG. 6 is an alternative embodiment having similar componentry to what was as previously described with reference to FIG. 4. In this embodiment, however, received infrared light transiting the diffraction grating 416 impinges not directly upon the CCD image sensor 418 of FIG. 4, but upon the photocathode of a third-generation image intensifier tube 620. Light from the image intensifier's luminescent anode projects onto a CCD image sensor 622. Data indicative of received intensity at each wavelength and reception fiber is encoded and transmitted to the image construction system 624.

Figure 7:
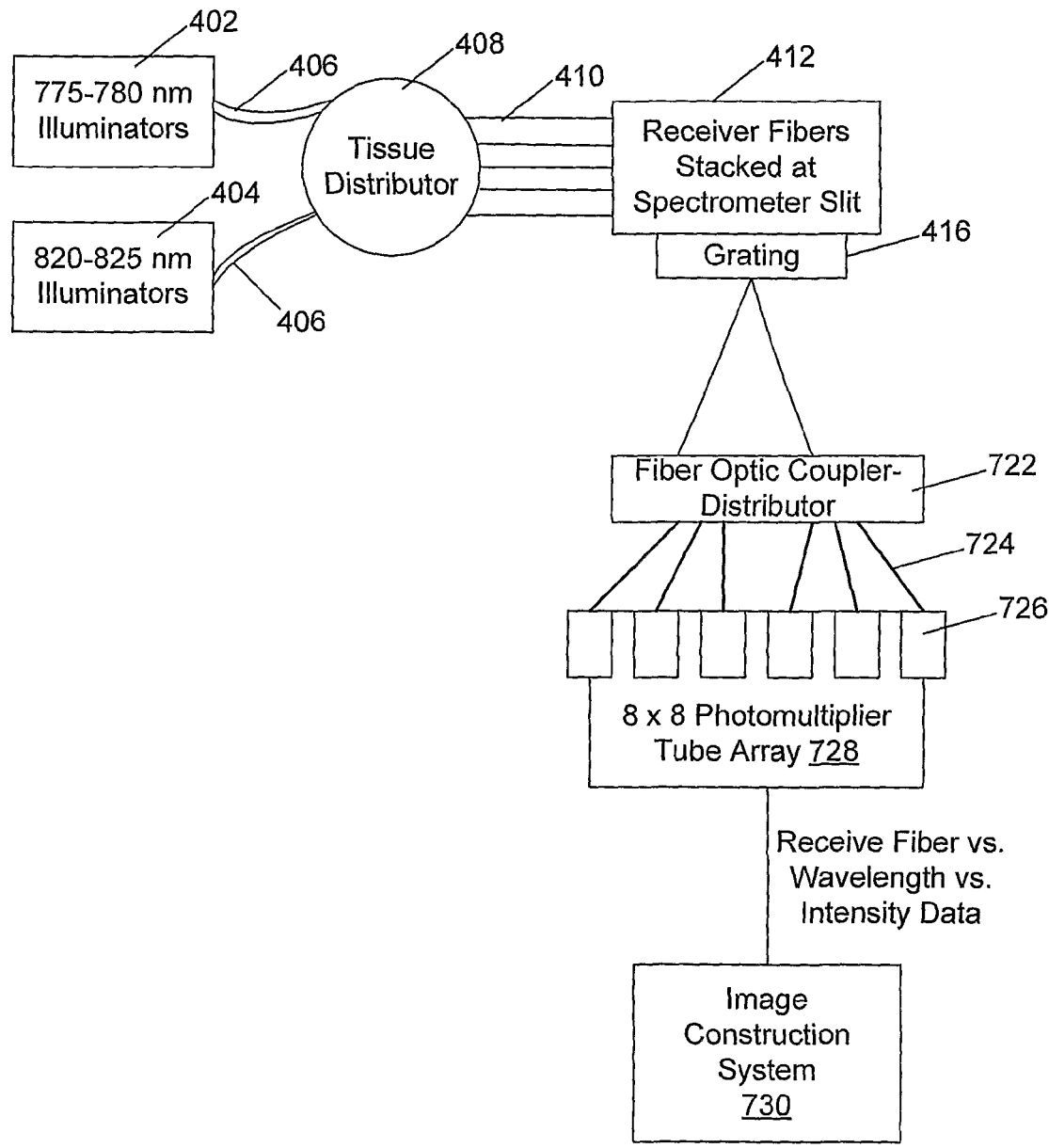
FIG. 7 is a block diagram of an embodiment incorporating a fiber-optic distributor and an array of photomultiplier tubes for improved weak-signal gain.

The embodiment illustrated in FIG. 7 is an alternative embodiment having similar componentry to what was previously described with reference to FIG. 4. In this embodiment, however, received infrared light transiting the diffraction grating 416 impinges not directly upon the CCD image sensor 418 of FIG. 4, but upon the fibers of a fiber-optic coupler and distribution apparatus 722. Fiber-optic coupler and distribution apparatus 722 distributes light received from each combination of receive fiber 410 and wavelength through distribution fibers 724 into a separate photomultiplier tube 726 of photomultiplier tube array 728. In a monochrome embodiment, photomultiplier tube array 728 is an eight by eight (64-tube) array, while in a dichromatic embodiment, photomultiplier tube array 728 is a 128-tube array. Data from the photomultiplier tube array 728 indicative of received intensity at each wavelength and reception fiber is encoded and transmitted to the image construction system 730.

Figure 8:
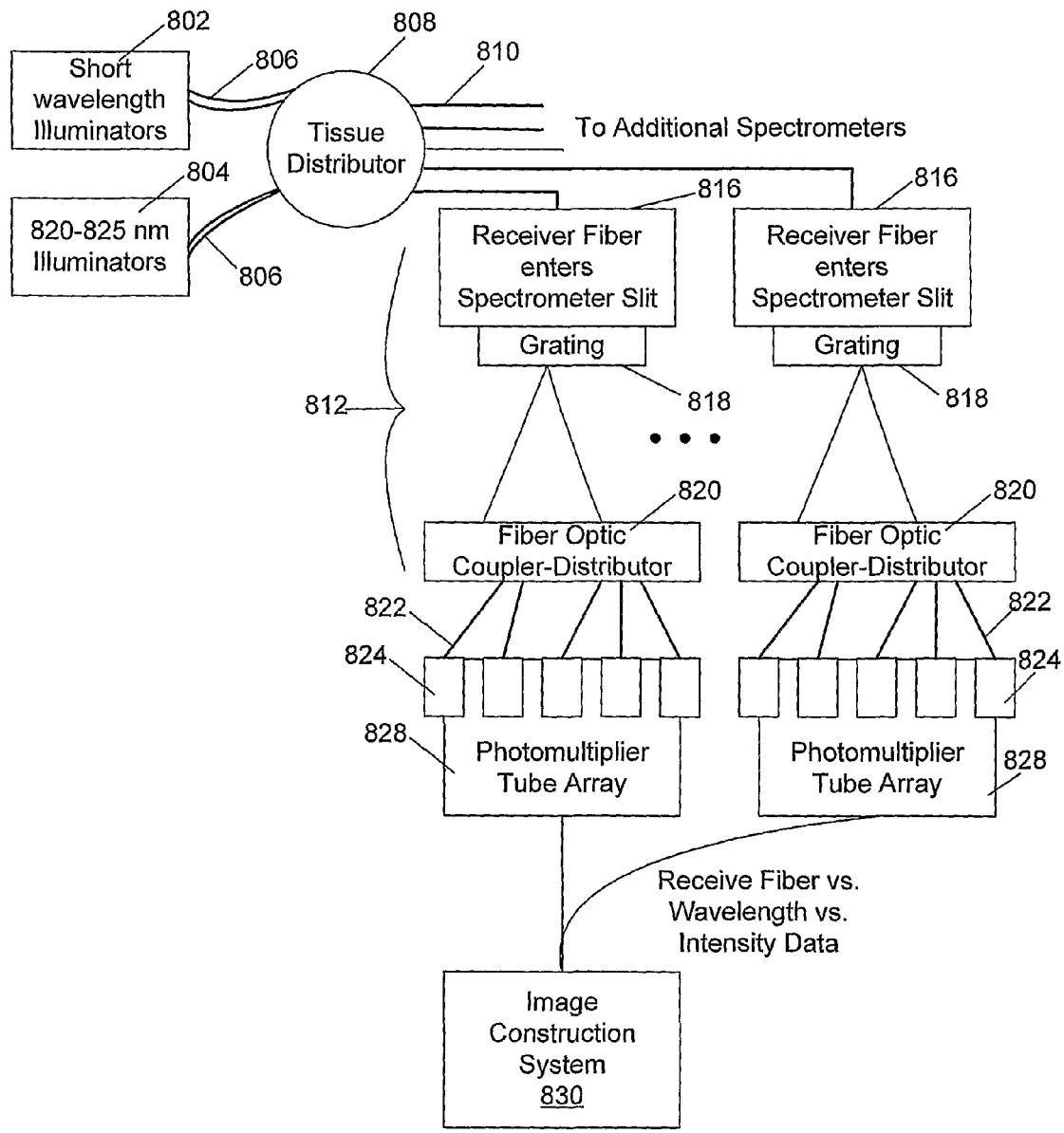
FIG. 8 is a block diagram of an alternative embodiment incorporating multiple spectrometers with an array of photomultiplier tubes.

The embodiment illustrated in FIG. 8 is an alternative embodiment having short-wavelength lasers 802, long wavelength lasers 804, transmit fibers 806, and tissue distributor 808 as previously described with reference to FIG. 4. Receive fibers 810, however, distribute received light to multiple spectrometers 812, such that each receive fiber feeds one spectrometer 812. In this embodiment, received infrared light from at least one receive fiber enters a slit 816 of each spectrometer 812, then transits the associated diffraction grating 818. This light is projected upon fibers of a fiber-optic coupler and distribution apparatus 820 for each spectrometer 812. Fiber-optic coupler and distribution apparatus 820 distributes light received as the wavelength associated with illumination lasers 802, 804 through distribution fibers 822 into a separate photomultiplier tube 824 of photomultiplier tube array 828. In a monochrome embodiment, photomultiplier tube array 828 is an eight tube array for each spectrometer, in a dichrome embodiment photomultiplier tube array 828 is a sixteen tube array for each spectrometer. Data from the photomultiplier tube arrays 828 of all eight spectrometers 812, indicative of received intensity at each wavelength and reception fiber, is encoded and transmitted to the image construction system 830.

One embodiment of an optical imaging system includes a novel intravascular/intraluminal imaging device. The intravascular/intraluminal imaging device combines aspects of optical coherence tomography (OCT) and NIR diffuse optical tomography (NIR-DOT). OCT uses optical echoes of a low coherent infrared light source (normally around 1300 nm) directed at tissue to create high-resolution tomographic images. The axial resolution of OCT is on the order of about 2 to 30 µm depending on the spectral width of the source, and the lateral resolution of OCT is on the order of about 5 to 30 µm as determined by the beam waist. However, in vivo intravascular OCT imaging is generally deficient in functional information because it measures beck-reflected coherent light that is strongly influenced by blood interference and low tissue penetration (~1.5 mm). On the other hand, NIR-DOT between about 400 and 2500 nm identifies the chemical contents of biological specimens with high contrast, but is subject to low resolution as a result of diffuse light detection. This non-linear transport leads to a hypersensitivity to the boundary, thus small errors in the measurement can significantly degrade the performance of NIR-DOT by introducing artifacts within the edge of the reconstructed image.

The intravascular/intraluminal imaging device described herein combines the high-resolution structural imaging capability of OCT with the abundant chemical information of NIR-DOT to provide both high resolution morphology and high-contrast functional information. The imaging device includes a catheter-based probe that may be used for imaging atherosclerotic plaque, endourologic detection of prostate cancer, analysis of aortic dissection and numerous other applications. The intravascular/intraluminal imaging device may further include a wire for indicating the device location by X-ray radiography, a lumen for delivery of contrast agents, and/or a balloon for angioplasty. Additionally, the imaging device may be used in combination with an endoscope.

Figure 9:
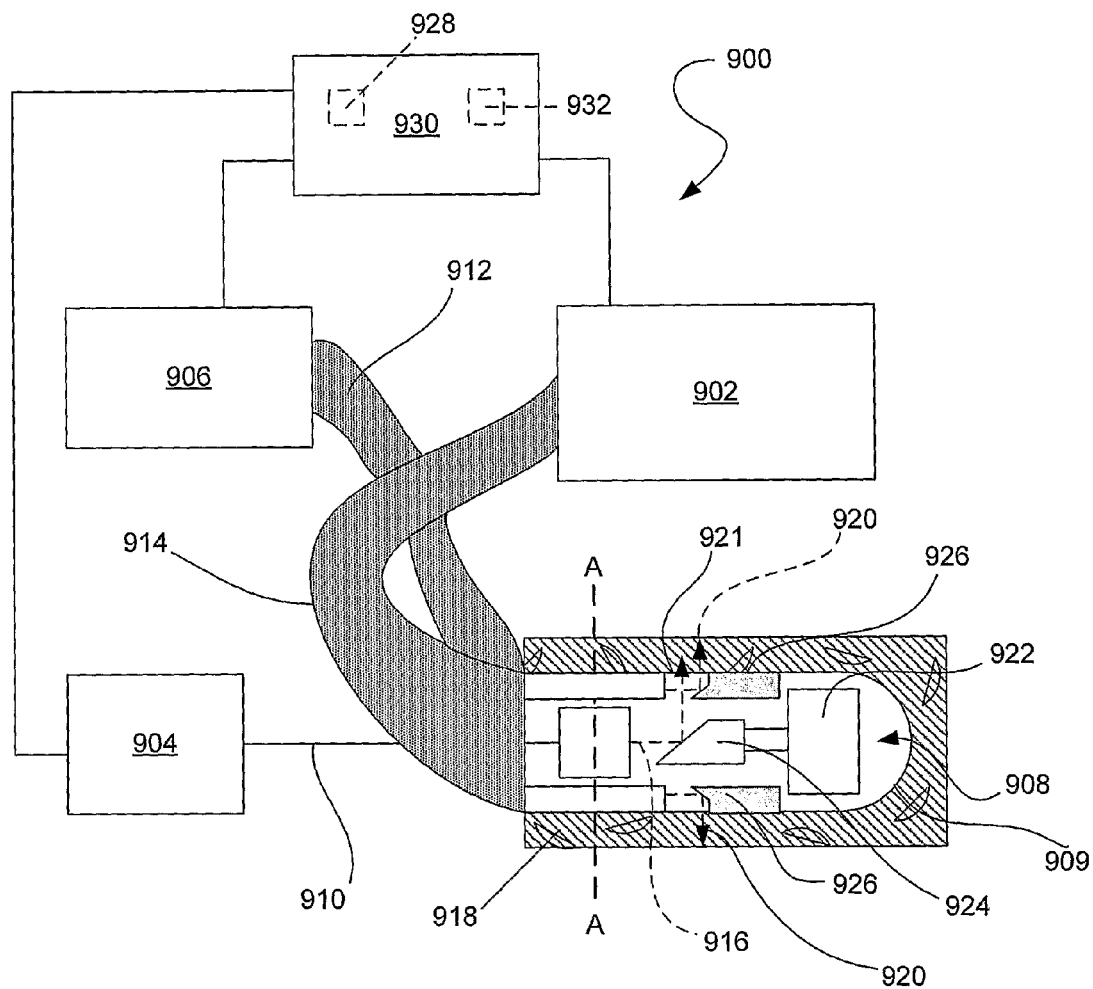
FIG. 9 illustrates an intravascular imaging device according to an embodiment.
Figure 9:
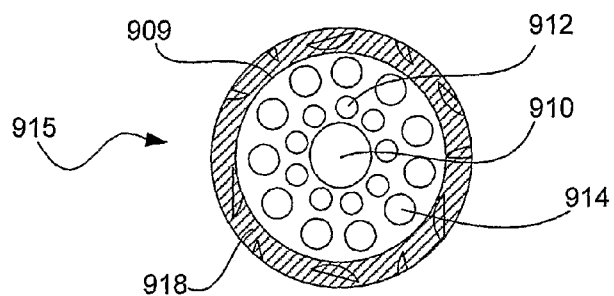

FIG. 9 (not to scale) illustrates an intravascular/intraluminal imaging device 900 that includes a spectrometer 902, an OCT unit 904, a NIR encoder 906 and a probe 908. Probe 908 includes a housing 909 having an OCT fiber 910 centrally disposed and a plurality of NIR fibers 912 and detector fibers 914 disposed peripherally around OCT fiber 910. A cross-section 915 of probe 908 along line A-A shows the fiber optic geometry. It will be understood that various modifications may be made to the above-described fiber optic geometry. OCT fiber 910 transmits signals 916 from OCT unit 904 to tissue 918. NIR fibers 912 transmit signals 920 from NIR encoder 906 to tissue 918, and detector fibers 914 transmit signals (not shown) from tissue 918 to spectrometer 902. OCT unit 904 provides high-resolution circumferential cross-sectional imaging by deflecting the probing light through a window 921 in housing 909 with a micromotor 922 driven 90-degree reflector 924, and NIR encoder 906 provides co-registered cross-sectional spectroscopic tomography by use of a novel spread-spectrum encoding-decoding technique and a stationary light reflector 926. A microprocessor 928 of computer 930 directs spectrometer 902, OCT unit 904, and NIR encoder 906 and stores data to memory 932.

Materials for use in the manufacture of external components of probe 908 should be biocompatible and approved by appropriate regulatory bodies, such as the Food and Drug Administration. Housing 909 may be manufactured, for example, of stainless steel, titanium and other metals, and polymers such as polyethylene, polytetrafluoroethylene (PTFE) (e.g., Teflon®), polyurethane, Dacron®, polyvinyl chloride, polystyrene and combinations thereof. Window 921 must be transparent to optical and NIR electromagnetic energy. Suitable materials for the manufacture of window 921 include, for example, quartz, polystyrene, polycarbonate and polypropylene.

Commercial spectrometers 902, OCT units 904, and NIR encoders 906 may be used in the construction of intravascular/intraluminal imaging device 900. For example, a Nicolet Fourier Transform Infrared Spectrometer produced by Thermo Electron Corporation of Waltham, Mass. may be used as spectrometer 902 and LightLab of Westford, Mass. manufactures a suitable OCT unit 904.

The intravascular/intraluminal imaging device may be used internally and/or externally in the detection and/or diagnosis of tumors, cysts, aneurysms, hematomas, and plaques in tissue including, for example, breast, brain, prostate, ovarian, uterine, cervical, colon, ureter, urethral, heart, liver, esophageal, skin and pancreatic.

In addition to the previously described systems and methods, the present disclosure provides a DCSR method that utilizes frequency-domain data, which provides a more complete data set and gives more accurate images than when a continuous-wave approach is used. The disclosed DCSR methods may also be utilized in conjunction with the presently disclosed Spectral Derivative Image Reconstruction (SDIR) method.

SDIR is a method for multiwavelength diffuse optical tomography, where instead of using data from each wavelength separately or even simultaneously, the difference in data intensity for multiple wavelength pairs is used. See, Xu, H.; Pogue, B. W.; Springett, R.; Dehghani, H. "Spectral Derivative Based Image Reconstruction Provides Inherent Insensitivity to Coupling and Geometric Errors" Optics Letters, in press, (2005). Errors due to fiber and tissue coupling or external boundaries have a broadband offset effect, which is largely wavelength independent. Therefore, by taking the difference of data collected at two adequately spaced wavelengths, these common errors largely cancel, with the remaining signal containing the required chromophore and scatterer information. By properly choosing wavelength pairs, spatial resolution may be improved and crosstalk between chromophores of interest minimized. SDIR may reduce image artifacts in multispectral diffuse tomography, because coupling and boundary errors may be effectively removed in the data set of the first derivative of intensity with respect to wavelength while spectral information related to chromophores and scattering is retained. A first order approach to the finite differencing is presented herein, but the model may be adapted to higher order approaches.

A potential advantage of SDIR is that only intensity measurement is required at each wavelength so that the hardware implementation can be a continuous-wave laser system or a steady-state broadband system without using a complex frequency or time domain system that provides secondary measurement to an optical pathlength. It will be appreciated, however, that frequency-domain methods may also benefit from SDIR.

The first derivative or finite difference approach of SDIR can be used with multiple imaging algorithms (e.g., both continuous wave and frequency-domain DCSR) on data collected using various instruments in the diagnosis and/or treatment of a wide variety of diseases. For example, SDIR may be used to generate images useful in the diagnosis and/or treatment of breast cancer, brain cancer, prostate cancer, aneurysms, hematomas, tumors, cysts, heart disease, renal artery stenosis, peripheral vascular disease, and vulnerable plaques. Imaging may be performed prior to and/or during an invasive procedure.

Figure 10:
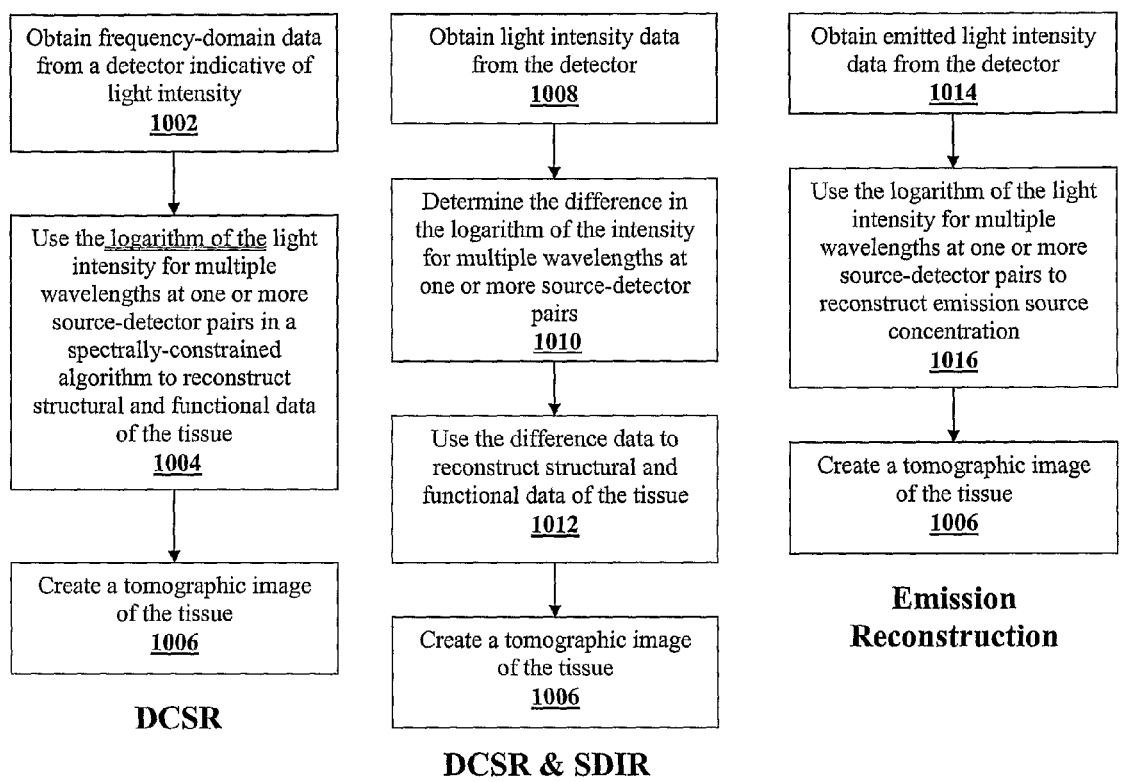
FIG. 10 is a flowchart illustrating steps for obtaining and reconstructing images using multispectral methods.

FIG. 10 is a flowchart illustrating steps for obtaining and reconstructing images using multispectral methods. The DCSR method involves obtaining 1002 frequency-domain data from a detector indicative of light intensity. Using 1004 the logarithm of the light intensity for multiple wavelengths at one or more source-detector pairs in a spectrally-constrained algorithm to reconstruct structural and functional data of the tissue, and creating 1006 a tomographic image of the tissue. When the SDIR method is used in conjunction with the DCSR method, light intensity data is obtained 1008 from the detector, the difference in the logarithm of the intensity for multiple wavelengths at one or more source-detector pairs is determined 1010, the difference data is used 1012 to reconstruct structural and functional data of the tissue, and a tomographic image of the tissue is created 1006. For detection of emission sources, no excitation light source is required. Emitted light is detected by the detector and light intensity data is obtained 1014 from the detector. The logarithm of the light intensity for multiple wavelengths at one or more source-detector pairs is used 1016 to reconstruct emission source concentration. The emission source concentration data are then used to create 1006 a tomographic image of the tissue. In all cases, concentrations are determined by Beer's Law:

$$A=\epsilon bc$$

where A is absorption, $\epsilon$ is the molar absorbtivity coefficient ($M^{-1}$ $cm^{-1}$), b is the pathlength measured in centimeters, and c is the concentration in units of molarity.

Example 1

Intravascular Imaging Device Construction

An intravascular imaging device, according to an embodiment, includes spectrometer 902, OCT unit 904, NIR encoder 906, and combined OCT/NIR tomographic spectroscopy probe 908. Probe 908 is about 2 mm in diameter and includes a central OCT fiber 910 and a plurality of NIR imaging fibers 912 and detector fibers 914 distributed around the periphery of OCT fiber 910. OCT unit 904 is a conventional time-domain configuration, and the intravascular circumferential cross-sectional imaging is achieved by the rotation of a micromotor 922 driven 90-degree reflector 924 that eliminates axial rotation of probe 908. An imaging frame rate of 4 Hz is used. NIR encoder 906 incorporates a spread-spectrum encoding-decoding technique. Diffuse tomographic imaging requires information from multiple source-detector pairs, and current approaches of decoding the multiple source-detector pairs either limit the imaging speed or limit the dynamic range of the detection. In spread-spectrum encoding, the collimated emission of a high-power low-coherence source (such as LEDs with spectral-width of about 30 nm and power of several hundred milliwatts) is dispersed by a diffraction grating and collimated to a linear fiber bundle 912. Light sources with different center wavelengths can be dispersed by the same grating and focused to the same linear fiber bundle 912. The linear fiber bundle 912 delivers the spread-spectrum encoded light to probe 908, where the fiber bundle is arranged in a circular geometry (see cross-section 915). The lights from the circularly distributed fiber array 912 are reflected by a circular 90-degree reflector 926 to the vessel wall. The diffused photons are reflected by the same circular 90 degree reflector 926 and detected by the detector fiber array 914 that is also displaced in a circular geometry and co-centric to the NIR fiber array 912 (see cross-section 915). The detected light is then delivered to spectrometer 902 where the detector fiber bundle 914 becomes linear again, and signals 920 from spread-spectrum-encoded sources are separated for parallel decoding and detection from all source-detector pairs. With this technique, 16 source fibers of 100 μm and 16 detector fibers of 200 μm can be arranged inside the 2 mm catheter probe 908, resulting in a total of 256 pairs of optodes (i.e., source-detector pairs).

Four LEDs, having 30 nm bandwidth each, are incorporated into the presently described design with center wavelengths of 700 nm, 760 nm, 850 nm and 940 nm. Spectrometer 902 is able to resolve a 300 nm total range; therefore, the signals from each source cover about 1/10 of the total range. For a CCD detector of 512×512 pixels, 1/10 of the CCD width, which is 50 pixels, is sufficient to decode the signals from 16 source fibers.

The tomographic reconstruction of the NIR spectroscopic data is performed based on a Monte-Carlo model that deals with very short source-detector distances and superficial photon migrations. Since the size of the intravascular probe is 2 mm, the longest distance between source and detector along the circumference is about 6 mm, therefore, a NIR imaging depth of 3 mm is achieved. This is about twice as much as that of OCT. In terms of the image resolution of NIR tomography, 1×1 $mm^2$ produces about 50 pixels in the reconstructed image.

Example 2

Intravascular Imaging Method

An intravascular imaging device may be used to detect atherosclerotic cardiovascular disease by measuring the extent of plaque or measuring the extent and depth of ischemia in a catheterization procedure. The patient receives a mild sedative such as Midazolam approximately 30 minutes before the procedure. The groin, neck or forearm is cleansed with a sterilizing solution, shaved, and covered with a sterile drape. A local anesthetic is used to numb the area before a small incision is made and a sheath is inserted into the artery (e.g., femoral artery, carotid artery) or vein. The probe of the intravascular imaging device is passed through the sheath and threaded to the aorta, coronary artery and/or left ventricle of the heart. During probe insertion, probe location is monitored using an X-ray machine that produces real-time images (fluoroscopy) and a radio-opaque wire within the probe.

Once the probe is in place, OCT and NIR signals at multiple wavelengths are sent sequentially to the probe. The return signals are sent to the spectrometer and results are saved in a computer memory. A second and subsequent set of data is collected by moving the probe a short distance and repeating the illumination/detection protocol. A microprocessor manipulates the raw data using SDIR algorithms and creates a three-dimensional tomographic image that may be viewed in real time on a display.

Example 3

Direct Chromophore Spectral Reconstruction and Spectral Derivative Image Reconstruction The general diffuse optical tomography (DOT) reconstruction algorithm is based on a standard least squares error optimization, where the recovery of $\mu_a$ and $\mu'_s$ distribution is based on measurements of light fluence at the tissue surface. The inverse solution is achieved by minimizing the difference between measured (observed) fluence $\Phi^o$ at the tissue surface and calculated data $\Phi^c$ from a given model. This is a minimization of $\Psi$:

$$\Psi = \|\Phi_{\lambda_1}^c(x) - \Phi_{\lambda_1}^o\|_2^2 \tag{1}$$

Where column vectors $\Phi_{\lambda_1}^c$ and $\Phi_{\lambda_1}^o$ represent calculated and measure fluence at all the source-detector pairs at wavelength $\lambda_1$. Vector x is the unknown parameter and is the spatially distributed optical properties, $x=[\mu_a(\lambda_1)\mu'_s(\lambda_1)]$. Equation 1 can be reformulated into a method to recover the chromophore, fluorophore and/or bioluminescent source data directly by use of multiple wavelengths of emission data. This is called the Direct Chromophore Spectral Reconstruction (DCSR) method. The DCSR method is based on two principles. First, that the wavelength dependent absorption is a linear combination of absorbing components in the tissue, $\mu_a(\lambda_1) = \Sigma_i \epsilon_i(\lambda) c_i$, where $\epsilon_i$ is the specific extinction coefficient and $c_i$ is the concentration map of $i^{th}$ chromophore. Second, the wavelength dependence of reduced scattering is modeled by an empirical approximation, $\mu'_s(\lambda) = a(\lambda/\lambda_0)^{-b}$, where $\lambda_o$ is a normalization wavelength. A useful setting is $\lambda_o = 1$ µm, when near-infrared wavelengths are used. The unknown parameters $x=[a\ b\ c_1\ c_2\ c_3]$ are independent of $\lambda$ and therefore the measurement at multiple wavelengths can be coupled to yield a new objective function:

$$\Psi_1 = \|\Delta\Phi^{c-o}\|_2^2 = \left\| \begin{Bmatrix} \Phi_{\lambda_1}^c(x) \\ \Phi_{\lambda_2}^c(x) \\ \vdots \\ \Phi_{\lambda_m}^c(x) \end{Bmatrix} - \begin{Bmatrix} \Phi_{\lambda_1}^o \\ \Phi_{\lambda_2}^o \\ \vdots \\ \Phi_{\lambda_m}^o \end{Bmatrix} \right\|_2^2 \tag{2}$$

Image reconstruction with the objective function in Equation 2 is a useful way to directly recover chromophore concentrations, and constrain the concentration values in a way which fits with the known extinction coefficient spectra of the constituents of the tissue.

The iterative formula for converging to a solution can be derived as $\Delta x = (\Im^T \Im)^{-1} \Im^T \Delta\Phi^{c-o}$, where $\Im$ is the Jacobian matrix comprising the sensitivity for each parameter and the measurement at each wavelength:

$$\mathcal{J} = [\mathcal{J}_a \mathcal{J}_b \mathcal{J}_{c_1} \mathcal{J}_{c_2} \mathcal{J}_{c_3}] \tag{3}$$

$$= \begin{bmatrix} \mathcal{J}_{a,\lambda_1} & \mathcal{J}_{b,\lambda_1} & \mathcal{J}_{c_1,\lambda_1} & \mathcal{J}_{c_2,\lambda_1} & \mathcal{J}_{c_3,\lambda_1} \\ \mathcal{J}_{a,\lambda_2} & \mathcal{J}_{b,\lambda_2} & \mathcal{J}_{c_1,\lambda_1} & \mathcal{J}_{c_2,\lambda_2} & \mathcal{J}_{c_3,\lambda_2} \\ \vdots & \vdots & \vdots & \vdots & \vdots \\ \mathcal{J}_{a,\lambda_m} & \mathcal{J}_{b,\lambda_m} & \mathcal{J}_{c_1,\lambda_m} & \mathcal{J}_{c_2,\lambda_m} & \mathcal{J}_{c_3,\lambda_m} \end{bmatrix}$$

Alternatively, instead of using each wavelength of emission data as is, a spectral derivative data set can be created from the difference in logarithm of intensity emitted at each wavelength. This is called the Spectral Derivative Image Reconstruction (SDIR).

In the SDIR approach, the objective function is modified from Equation 2:

$$\Psi_2 = \|\Delta\Phi'^{c-o}\|_2^2 = \left\| \begin{Bmatrix} \Phi_{\lambda_1}^c(x) - \Phi_{\lambda_2}^c(x) \\ \Phi_{\lambda_2}^c(x) - \Phi_{\lambda_3}^c(x) \\ \vdots \\ \Phi_{\lambda_{m-1}}^c(x) - \Phi_{\lambda_m}^c(x) \end{Bmatrix} - \begin{Bmatrix} \Phi_{\lambda_1}^o - \Phi_{\lambda_2}^o \\ \Phi_{\lambda_2}^o - \Phi_{\lambda_3}^o \\ \vdots \\ \Phi_{\lambda_{m-1}}^o - \Phi_{\lambda_m}^o \end{Bmatrix} \right\|_2^2 \tag{4}$$

Here the prime denotes the finite difference operator to remind one of the similarity between derivative and finite difference. The Jacobian matrix for SDIR can be derived from the Jacobian calculated using the conventional method and is the subtraction of the first m−1 row and the last m−1 row of $\Im$ in Equation 3. The sequence of pairs of wavelengths used in Equation 4 can be arbitrary, for example one can use $\{[\lambda_1, \lambda_2], [\lambda_1, \lambda_3], \ldots\}$ or $\{[\lambda_1, \lambda_2][\lambda_2, \lambda_3], \ldots\}$ Equation 4 is useful, for example, where coupling coefficient error exists in the measurement so that measured intensity $I^o$ is the product of the coupling efficiency k and the real intensity $I^r$, $I^o = kI^r$, since typically in the model $\Phi^o = \log(I^o) = \log(I^r) + \log(k)$, the coupling error becomes an additive term. Using this measurement with coupling error, the SDIR algorithm (Equation 4) will not be affected, but Equations 1 and 2 treat the coupling error as part of the real signal and will lead to image artifacts.

The Jacobian matrix is a function of the wavelength pairs chosen. If wavelength pairs are chosen where higher absorbance contrast can be achieved for chromophores, more sensitive and independent sub-Jacobian matrices ($\Im_a, \Im_b, \Im_{c1}, \Im_{c2}, \Im_{c3}$) can be constructed to provide better separation and localization of chromophore concentrations.

Computational analysis of the algorithms described above is performed by image construction system 130, 422, 624, 730.

Example 4

Multispectral Image Reconstruction of Hemoglobin, Oxygen Saturation and Water Fraction in Tissue In the multispectral DCSR approach to image reconstruction, the possible spectral shapes of the chromophore and scattering models are implemented into the image formation process, thereby adding a spectral constraint into the reconstruction. This type of reconstruction uses multiwavelength measurements simultaneously to estimate images of oxyhemoglobin, deoxyhemoglobin, water and scatter parameters directly, without intermediate recovery of optical properties. Assuming the main absorbers in the tissue are oxyhemoglobin ($HbO_2$), deoxyhemoglobin (Hb) and water and knowing their molar absorption spectra (absorption per unit concentration) at the observed wavelengths, it is possible to calculate each of their contributions to the absorption at various points in the tissue. Images representing a map of $HbO_2$, Hb, and the ratio of $HbO_2$ to Hb contributions to absorption are presented to a user of the system to permit diagnosis.

Relationships from Equations 3 and 4 form the basis of the spectral approach to image reconstruction, which involves direct recovery of images of the concentrations of $HbO_2$, Hb and water and scatter amplitude and power by coupling multiwavelength measurements together. This approach also uses Newton's method along with the Levenberg-Marquardt regularization, but the minimization includes the measurements from all observed wavelengths. The least squares function is rewritten as $$\chi^2 = \sum_{j=1}^{Mn} (\phi_j^m - \phi_j^c)^2,$$

so that the sum includes all wavelength measurements (Mn), where n is the number of wavelengths available. The relationship for each wavelength, with the spectral constraints included, is represented by $$\partial \phi_\lambda = \Im_{c,\lambda} dc + \Im_{A,\lambda} dA + \Im_{b,\lambda} db, \quad (5)$$

where $\Im_{c,\lambda}$, $\Im_{A,\lambda}$ and $\Im_{b,\lambda}$ represent the Jacobians for each of the chromophore and scattering parameters and the update occurs in terms of the chromophores, $\partial c$, directly:

$$(\tilde{\Im}^T \tilde{\Im} + \alpha I) \partial c = \tilde{\Im}^T \partial \phi, \quad (6)$$

where $\partial \phi = (\phi^{m,\lambda} - \phi_k^{c,\lambda})_{\lambda=1:n}$ and $\tilde{\Im} = [\Im_{c,\lambda}, \Im_{A,\lambda}, \Im_{b,\lambda}]_{\lambda=1:n}$ and $\alpha$ is the regularization parameter. The technique reduces the total number of unknown parameters in the image reconstruction (from number of wavelengths times optical properties to five parameters overall) and makes the inverse problem better posed by increasing the stability to noise in the measured data. The technique is optimized in terms of obtaining initial estimates of the parameters, regularization, convergence criteria, filtering and to allow for the best calibration procedure for the data. It has been validated in homogeneous imaging fields, simulations and experiments. The results indicate that higher qualitative and quantitative accuracy, as well as reduced crosstalk between the functional parameters, is achieved.

The spectrally constrained approach is inherently robust due to the addition of a priori spectral behavior, and requires less spatial filtering. In studies using simulated and experimental data, at 1% noise, which is a typical level found in tomography systems, the reduction in standard deviations in oxygen saturation, water and scatter power were significant. The trend was continued at 5% noise in the amplitude and phase data (5% is near the limit of data noise found in typical measurement systems). The spectrally constrained technique yields quantification accurate to within 15% of true values, whereas using the traditional method, high standard deviations make it impossible to obtain useful NIR information. There is a significant reduction in the crosstalk between oxy-hemoglobin and water, due to prior knowledge of the spectral shapes, as well as with deoxyhemoglobin and scatter parameters. These constraints are also responsible for the robust nature of the method to higher levels of noise as compared to traditional methods.

Figure 11:
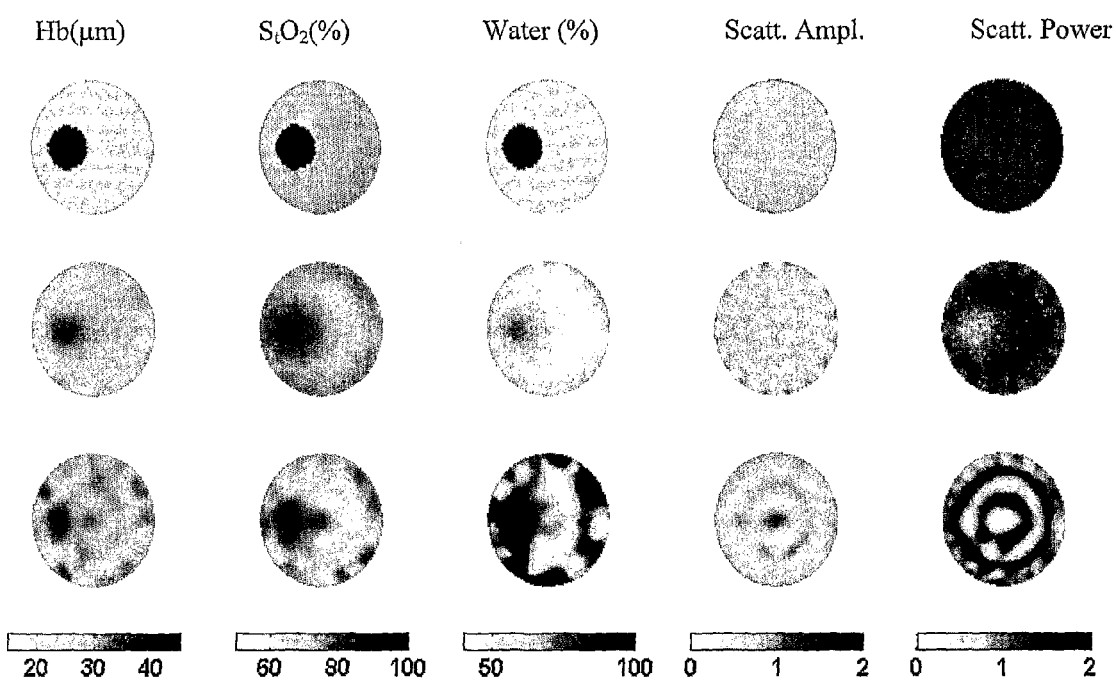
FIG. 11 is a simulation data set with a localized region of increased hemoglobin, oxygen saturation, and water.

FIG. 11 shows a simulation data set with a localized region of increased hemoglobin, oxygen saturation, and water in a region left of center, with homogeneous scattering amplitude and scattering power. The tissue phantoms are shown in the top row of images. Images resulting from traditional reconstruction methods are shown in the bottom row. To obtain the traditional images, transmission data at six near-infrared wavelengths was generated with an average of 1% noise in amplitude. The data were used to recover images of the chromophores and scatterers. Reconstruction of the six wavelengths was performed to determine absorption and scattering coefficients separately and then the data were fit for the values of Hb, $S_tO_2$, water and scattering amplitude and power. Using the DCSR approach, where all wavelengths are reconstructed together, the images shown in the middle row resulted. The DCSR approach provided fewer image artifacts and more accurate values of each parameter.

Figure 12:
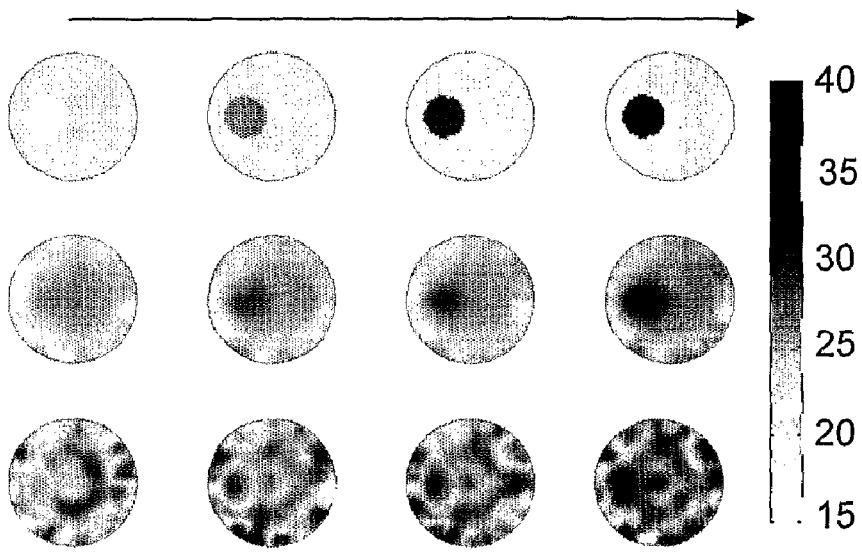
FIG. 12 is a reconstruction of phantoms with a single inclusion where the hemoglobin concentration and the scattering amplitude are systematically varied.
Figure 12:
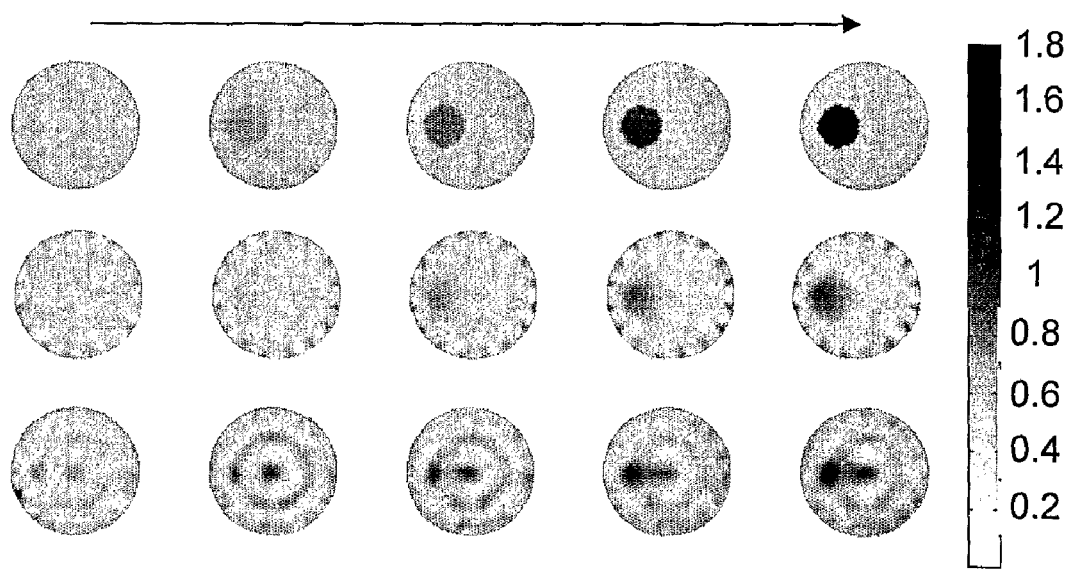

FIG. 12 shows reconstructions of phantoms with a single inclusion where the hemoglobin concentration and the scattering amplitude were systematically varied. Increasing hemoglobin concentration is shown in the upper series of images and increasing scattering amplitude is shown in the lower series of images. Again, a representation of the true phantom images is shown in the top row of each series. The DCSR images are shown in the middle row of each series, and the traditional, separate wavelength-approach images are shown in the bottom row of each series. These images of experimental data at different contrasts validates that the DCSR approach provides images which are closer to the true expected values.

Example 5

Spectral Derivative Image Reconstruction of Hemoglobin

The SDIR method may overcome several inherent measurement errors such as coupling coefficient variation, boundary reflection mismatch and geometric mismodeling. The difference or derivative spectrum is used to cancel the common error term seen at each wavelength while maintaining the scattering and chromophore spectral and spatial contrast. SDIR may be adapted to various imaging modalities where multispectral information is available.

Figure 13:
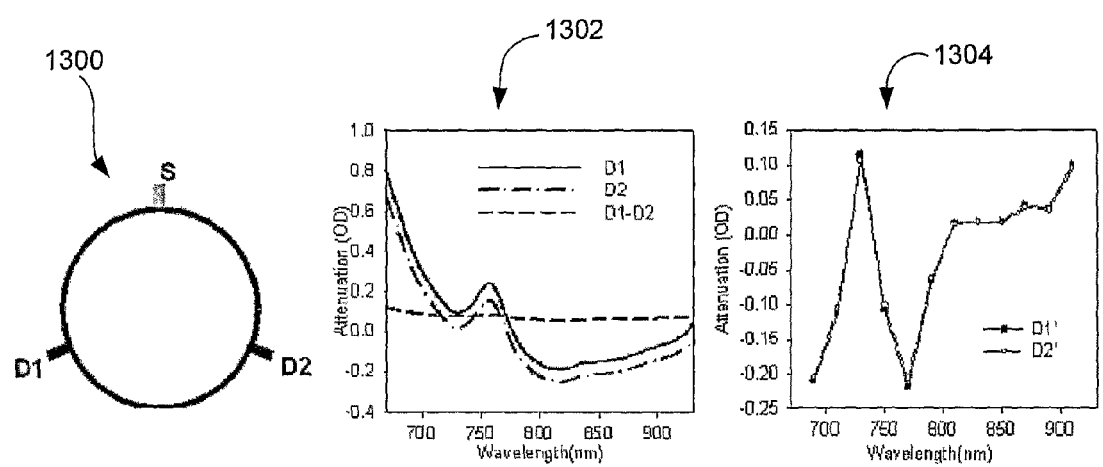
FIG. 13 is an experimental setup and graphs of resulting spectra and first order finite difference spectra resulting therefrom.

FIG. 13 shows an experimental setup and graphs of resulting spectra and first order finite difference spectra resulting from the illustrated setup. Experimental setup 1300 shows positions of a source S and detectors D1, D2, where source-detector pairs, e.g., S-D1 and S-D2, may be formed by the combination of one source and one detector. It will be appreciated that multiple sources may be present (S1, S2 ... Sn) and that source-detector pairs may also be formed by substituting one source for another, e.g., S1-D1, S2-D2. The illustrated geometry was used to measure a homogeneous diffuse blood phantom using a broadband NIR tomography system. Graph 1302 shows measured attenuation spectra at D1 and D2, and their difference (D1-D2). Ideally, the spectra of the symmetric detectors for a symmetric homogeneous phantom should overlap precisely, but in reality small differences are seen due to the different coupling coefficient as a function of the contact fibers on the phantom surface. Graph 1304 shows the first order finite difference spectra of D1 and D2 at two wavelengths that are separated by 20 nm. As shown, finite difference spectra display less error than spectra from identically situated detectors. This experiment confirms that SDIR can remove artifacts related to coupling coefficients.

Figure 14:
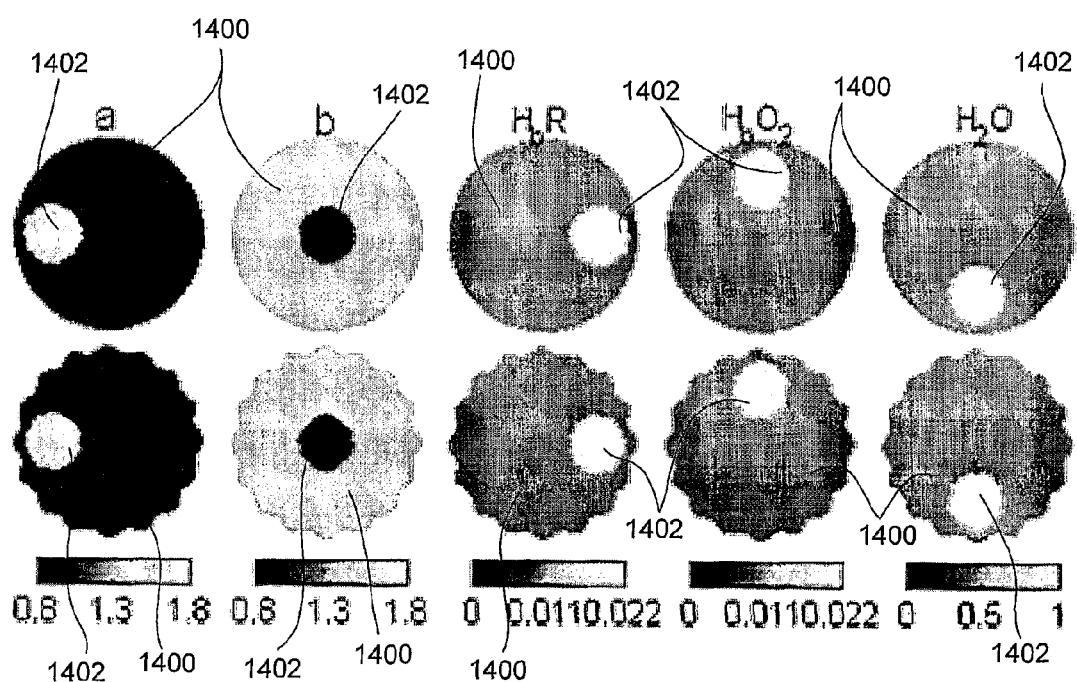
FIG. 14 shows phantoms with five distinct inclusions.

FIG. 14 shows phantoms 1400 with five distinct inclusions 1402. The five inclusions 1402 are denoted in the column headings as scattering amplitude, a; scattering power, b; deoxyhemoglobin concentration, $[H_bR]$; oxyhemoglobin concentration, $[H_bO_2]$; and water concentration, $[H_2O]$. Phantoms 1400 for this experiment have a total diameter of 27 mm and background and inclusion parameters as shown in Table 1:

TABLE 1

Parameters for background medium and inclusions of FIG. 14.

|  | $a(10^{-3b} mm^{b-1})$ | b | $[H_bR]$ (μM) | $[H_bO_2]$ (μM) | $[H_2O]$ |
|---|---|---|---|---|---|
| Background | 1.0 | 1.4 | 0.01 | 0.01 | 0.5 |
| Inclusions | 1.5 | 1.0 | 0.02 | 0.02 | 1 |

Data measured at 13 wavelengths from 670 nm to 910 nm, in 20 nm increments, were simulated for a linear triangular mesh with 425 nodes, having an equally distributed set of 8 sources and 8 detectors around the boundary. Only intensity measurement was considered. A half percent of Gaussian random noise was added to all synthesized data. The lower row illustrates phantoms 1400 where 5% Gaussian coupling coefficient error was added to the data shown in the upper row.

Figure 15:
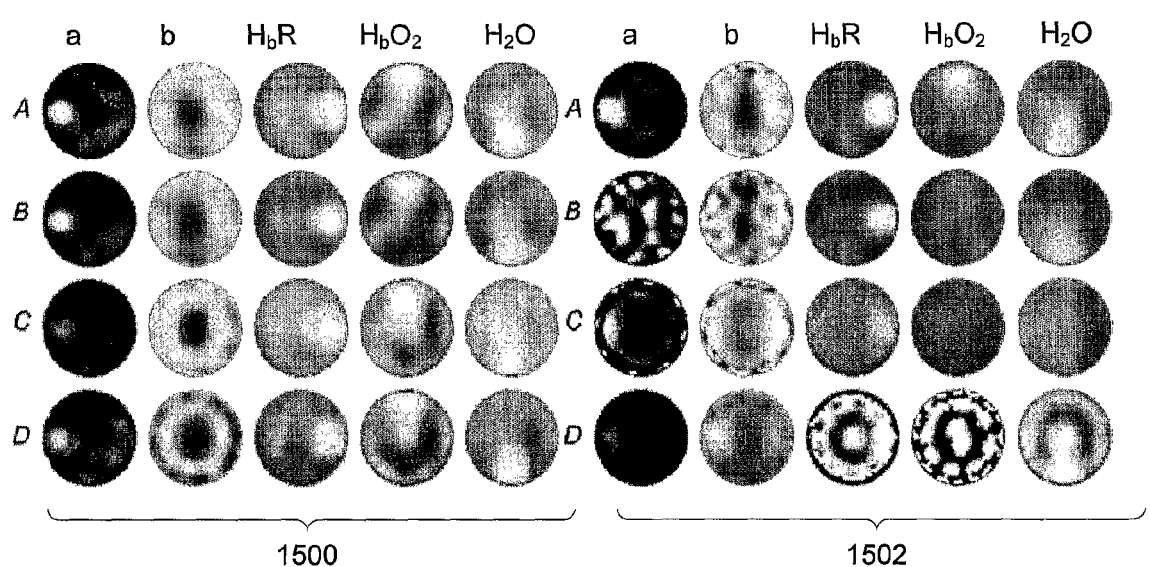
FIG. 15 compares images of liquid tissue-simulating phantoms obtained by Spectral Derivative Image Reconstruction (SDIR) and Direct Chromophore Spectral Reconstruction (DCSR).

FIG. 15 compares images of liquid tissue-simulating phantoms 1400 (FIG. 14) obtained by Spectral Derivative Image Reconstruction (SDIR) and Direct Chromophore Spectral Reconstruction (DCSR). The left hand block of images (corresponding to bracket 1500) shows SDIR images; the right hand block of images (corresponding to bracket 1502) shows DCSR images. Row A shows images with no data error; Row B has 5% randomly distributed data error; Row C includes boundary reflection coefficient modeling errors; and Row D reconstructs data taken from a distorted boundary shape. Normalized RMS error of each reconstructed image is shown in Table 2, where all values shown are percentages.

TABLE 2

Comparison of normalized RMS error between SDIR and DCSR images.

| | SDIR | | | | | DCSR | | | | |
|---|---|---|---|---|---|---|---|---|---|---|
| Row | a | b | $[H_bR]$ | $[H_bO_2]$ | $[H_2O]$ | a | B | $[H_bR]$ | $[H_bO_2]$ | $[H_2O]$ |
| A | 11.2 | 11.1 | 15.2 | 17.3 | 18.4 | 8.2 | 10.3 | 13.0 | 19.4 | 17.8 |
| B | 11.2 | 11.1 | 15.2 | 17.3 | 18.4 | 31.5 | 16.0 | 16.1 | 22.2 | 21.3 |
| C | 17.2 | 7.1 | 15.1 | 14.3 | 16.5 | 23.5 | 18.3 | 21.5 | 29.1 | 26.0 |
| D | 12.6 | 7.4 | 14.8 | 17.0 | 16.6 | 23.5 | 15.6 | 90.9 | 527.4 | 22.2 |

Columns a, b, $[H_bR]$, $[H_bO_2]$, and $[H_2O]$ correspond to the labeled columns in FIGS. 14 and 15. In this simulation, the SDIR model shows higher tolerance than the DCSR model to errors in absolute intensity measurement, and reduces reconstructed artifacts. SDIR also reduces parameter crosstalk and improves quantitative accuracy, giving increased sensitivity for oxyhemoglobin within a differential spectrum.

Example 6

Multispectral Bioluminescence Tomography

Tissue may be treated with a medical imaging composition, such as luciferase, that causes light emission at one or more points in the tissue. Measurements of the spectrum of the light intensity at the tissue surface are recorded using a spectrometer. These multispectral measurements can be used with the DCSR method as well as with the SDIR method to reconstruct the size, location and intensity of the bioluminescence source within the volume. The emitted light is attenuated differently at each wavelength, and by incorporating a reconstruction approach that uses all wavelengths together, there is an improved ability to accurately reconstruct the source strength and distribution.

Emitted light from firefly luciferase is a widely distributed band of wavelengths from 500 nm up to above 650 nm. When not attenuated, it has a peak emission near 560 nm, but when detected from within an animal appears to have a peak near 600 nm with measurable emissions of up to 50 nm above and below this peak. It is possible to measure the emission at the surface of the tissue in discrete steps of, for example, 10 nm ranging from between 550 nm and 650 nm, although strong optical absorption at the lower wavelengths may hinder accurate measurements with adequate signal to noise.

The data can be represented by an operator, which is linear in terms of the bioluminescence source. For simplicity, it is assumed that absorption and scatter parameters are known; they can be calculated using NIR data. The image reconstruction method is posed as a solution to the following minimization expression:

$$\chi^2 = (y - F(B))^2 \qquad (7)$$

where y is the measured data, F is the forward model calculated with bioluminescence source B(r). A practical approach to solving this problem is generally developed by assuming that the solution to this equation can be computed assuming a linear model by creating a set of independent basis solutions for the source, $$B = \sum_{i=1}^{N} a_i b_i,$$

where the coefficients $a_i$ are the weight functions for multiple sources $b_i$ at all nodes i in the model containing a total number of nodes in the image. This can be represented in matrix form as, B=b A, where b is a matrix of size N×N and A is a vector of length N. Each column of matrix b is a unit source point at each appropriate location, and each element of A represents the strength (or weight) of that source. The size of b is reduced, if a coarser basis is used for the source than that of the diffusion model. Solving this matrix equation for a, in a least square manner, results in a single step linear expression, $$a = W^T(WW^T + \lambda I)^{-1} y \qquad (8)$$

where W is a matrix containing the solution of the diffusion equation for all possible source positions N and y is the measured boundary flux. Here λ is a regularization parameter and I is the identity matrix. Although the Hessian matrix $WW^T$ is well conditioned and invertible, the use of λ becomes necessary with the presence of noise in the data, allowing the damping of noise within reconstructed images. Herein, λ=0.001% of the maximum of the diagonal of the Hessian.

Reconstructions of a two-dimensional circle of radius 20 mm were modeled as containing 20 μM total blood with 75% oxygen saturation and 60% water content. The scatter amplitude and power of the medium were assumed to both be equal to 1. The corresponding optical properties for a range of wavelengths, 600-650 nm, were used as for a small animal model, and were used to generate boundary data, for a single bioluminescence source of 5 mm diameter. A typical reconstructed image for only one individual wavelength results in a superficial blur.

The method of multiwavelength spectral bioluminescent tomography is such that instead of considering only data from a single wavelength, multiple data sets that are measured from the same domain containing the same bioluminescence distribution, over a range of usable wavelengths should be coupled and used. In this manner, $a=\tilde{W}^T(\tilde{W}\tilde{W}^T+\lambda I)^{-1}\tilde{y}$, where $\tilde{W}=[W_{\lambda 1}; W_{\lambda 2}; W_{\lambda 3}; \ldots ; W_{\lambda n}]$ is the weight matrix of all n number of wavelengths cascaded and $\tilde{y}=[y_{\lambda 1};y_{\lambda 2};y_{\lambda 3}; \ldots ;y_{\lambda n}]$ is the measured boundary data of all n number of wavelengths cascaded. The solution a will be a vector corresponding to the number of unknowns.

Images are reconstructed using a combination of multiple wavelengths. The use of only 2 sets of wavelengths dramatically improves the qualitative accuracy of the reconstructed image. The use of additional data sets ranging to 6 wavelength bands improves both the quantitative and qualitative accuracy of the reconstructed images. The location of the reconstructed anomaly when 6 wavelength bands are used is within 1 mm of the original target location.

To explore the linearity of the reconstructed bioluminescence versus the true strengths, a set of boundary data were simulated with varying relative bioluminescence strengths ranging from 1 to 80. Images were reconstructed using 6 sets of coupled multiwavelength data ranging from 600-650 nm and the maximum reconstructed value of bioluminescence versus actual value was plotted. There was a good linear correlation between the actual and reconstructed bioluminescence value. Thus, physiological or functional changes of biological tissue as a function of time may be accurately determined.

The above-described method may be utilized to quantify any emission source present in tissue. Such emission sources may, for example, be luminescent, fluorescent, and/or phosphorescent.

The changes described above, and others, may be made in the systems and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

This specification contains numerous citations to references such as patents, patent applications, and publications. Each is hereby incorporated by reference.

What is claimed is:

1. A tomography system, comprising:
a plurality of lasers of a first group, each laser of the first group for generating light of a distinct wavelength within a first wavelength band;
apparatus for simultaneously applying the light from lasers of the first group to mammalian tissue at a plurality of stimulus locations, such that the apparatus is configured to apply light from a first laser of the first group to a first stimulus location but not to a second stimulus location, and configured to apply light from a second laser of the first group to the second stimulus location but not the first stimulus location, the first stimulus location differing from the second stimulus location;
a plurality of lasers of a second group, each laser of the second group for generating light of a distinct wavelength within a second wavelength band not overlapping the first wavelength band, the lasers of the second group operable simultaneously with the lasers of the first group;
wherein the apparatus for applying light to mammalian tissue is further configured to apply light from a first laser of the second group to the first stimulus location but not to the second stimulus location, and configured to apply light from a second laser of the second group to the second stimulus location but not to the first stimulus location;
apparatus for collecting light from the mammalian tissue at a plurality of reception points;
apparatus for separating light received from the apparatus for collecting light according to a wavelength of the received light;
apparatus for generating path attenuation signals encoding received light amplitude information for each path from a stimulus location to each reception point at each wavelength corresponding to each laser of the plurality of lasers; and
image construction apparatus for receiving the path attenuation signals and for reconstructing a tomographic image of the mammalian tissue corresponding to oxygenation of the mammalian tissue.

2. The tomography system of claim 1 wherein the image construction apparatus comprises a processor configured to perform an image reconstruction procedure selected from the group consisting of Direct Chromophore Spectral Reconstruction (DCSR) and Spectral Derivative Image Reconstruction (SDIR).

3. The tomography system of claim 2 wherein the image reconstruction procedure is SDIR, and further is based upon differences in logarithms of detected intensities at each wavelength at each reception point.

4. The tomography system of claim 1, wherein the first wavelength band is of bandwidth less than one percent, and a center wavelength of the first wavelength band is separated from a center wavelength of the second wavelength band by between five and ten percent.

5. The tomography system of claim 4, wherein the apparatus for generating a path attenuation signal further comprises a diffraction grating, a fiber-optic distributor, and a plurality of photomultiplier tubes.

6. The tomography system of claim 4, wherein the first wavelength band is within the range 750 to 860 nanometers and wherein the apparatus for generating a path attenuation signal further comprises a diffraction grating and a charge-coupled device (CCD) image sensor.

7. The tomography system of claim 6, wherein the apparatus for generating a path attenuation signal further comprises an image intensifier tube for amplifying light separated according to wavelength by the diffraction grating and for providing amplified light to the CCD image sensor.

8. The tomography system of claim 1, wherein the first wavelength band is near infrared between 620 and 1000 nanometers.

9. The tomography system of claim 8, wherein the first wavelength band is within the range 750 to 860 nanometers.

10. The tomography system of claim 8, wherein the first wavelength band is of bandwidth less than two percent of its center wavelength.

11. The tomography system of claim 10, wherein the apparatus for separating light further comprises a diffraction grating and the apparatus for generating a path attenuation signal further comprises a fiber-optic distributor, and a plurality of photomultiplier tubes.

12. The tomography system of claim 10, wherein the apparatus for separating light further comprises a diffraction grating and the apparatus for generating a path attenuation signal further comprises a charge-coupled device (CCD) image sensor.

13. The tomography system of claim 12, wherein the apparatus for generating a path attenuation signal further comprises an image intensifier tube.

* * * * *

UNITED STATES PATENT AND TRADEMARK OFFICE
CERTIFICATE OF CORRECTION

PATENT NO. : 8,000,775 B2
APPLICATION NO. : 12/088845
DATED : August 16, 2011
INVENTOR(S) : Brian William Pogue et al.

It is certified that error appears in the above-identified patent and that said Letters Patent is hereby corrected as shown below:

Column 13, line 8, Eq. 1 " $\Psi = \|\Phi_{\lambda_1}{}^c(x) - \Phi_{\lambda_1}{}^o\|2^2$ " should read -- $\Psi = \|\Phi_{\lambda_1}^c(x) - \Phi_{\lambda_1}^o\|_2^2$ --;

line 10, " $\Phi_{\lambda_1}{}^c$ and $\Phi_{\lambda_1}{}^o$ " should read -- $\Phi_{\lambda_1}^c$ and $\Phi_{\lambda_1}^o$ --;

lines 54-60, Eq. 3

$$\Im = [\Im_a \Im_b \Im_{c_1} \Im_{c_2} \Im_{c_3}]$$

$$= \begin{bmatrix} \Im_{a,\lambda_1} & \Im_{b,\lambda_1} & \Im_{c_1,\lambda_1} & \Im_{c_2,\lambda_1} & \Im_{c_3,\lambda_1} \\ \Im_{a,\lambda_2} & \Im_{b,\lambda_2} & \Im_{c_1,\lambda_1} & \Im_{c_2,\lambda_2} & \Im_{c_3,\lambda_2} \\ \vdots & \vdots & \vdots & \vdots & \vdots \\ \Im_{a,\lambda_m} & \Im_{b,\lambda_m} & \Im_{c_1,\lambda_m} & \Im_{c_2,\lambda_m} & \Im_{c_3,\lambda_m} \end{bmatrix}$$

" should read $$\Im = [\Im_a \Im_b \Im_{c_1} \Im_{c_2} \Im_{c_3}]$$

$$= \begin{bmatrix} \Im_{a,\lambda_1} & \Im_{b,\lambda_1} & \Im_{c_1,\lambda_1} & \Im_{c_2,\lambda_1} & \Im_{c_3,\lambda_1} \\ \Im_{a,\lambda_2} & \Im_{b,\lambda_2} & \Im_{c_1,\lambda_2} & \Im_{c_2,\lambda_2} & \Im_{c_3,\lambda_2} \\ \vdots & \vdots & \vdots & \vdots & \vdots \\ \Im_{a,\lambda_m} & \Im_{b,\lambda_m} & \Im_{c_1,\lambda_m} & \Im_{c_2,\lambda_m} & \Im_{c_3,\lambda_m} \end{bmatrix}$$

--

Column 14, line 19, "$\{[\lambda_1, \lambda_2][\lambda_2, \lambda_3],...\}$" should read --$\{[\lambda_1, \lambda_2],[\lambda_2, \lambda_3],...\}$.--

Signed and Sealed this
Fifth Day of June, 2012

David J. Kappos
*Director of the United States Patent and Trademark Office*